(12) United States Patent
Nohilly et al.

(10) Patent No.: US 8,100,928 B2
(45) Date of Patent: Jan. 24, 2012

(54) MORCELLATOR WITH DETACHABLE HANDLE

(75) Inventors: Martin J. Nohilly, Murray Hill, NJ (US); Simon Cohn, Rutherford, NJ (US)

(73) Assignee: Ethicon, Inc., Somerville, NJ (US)

( * ) Notice: Subject to any disclaimer, the term of this patent is extended or adjusted under 35 U.S.C. 154(b) by 394 days.

(21) Appl. No.: 11/502,341

(22) Filed: Aug. 10, 2006

(65) Prior Publication Data

US 2008/0039884 A1   Feb. 14, 2008

(51) Int. Cl.
*A61B 17/32* (2006.01)

(52) U.S. Cl. ....................................... 606/180

(58) Field of Classification Search .............. 600/204, 600/284; 606/79, 127, 167–171, 173, 177–179, 606/180–181, 184–185, 190, 207; 604/22, 604/164
See application file for complete search history.

(56) References Cited

U.S. PATENT DOCUMENTS

| | | | | |
|---|---|---|---|---|
| 5,112,299 A | | 5/1992 | Pascaloff | 604/22 |
| 5,338,307 A | * | 8/1994 | Stephens et al. | 604/167.01 |
| 5,520,634 A | * | 5/1996 | Fox et al. | 604/22 |
| 5,538,509 A | * | 7/1996 | Dunlap et al. | 604/264 |
| 5,562,694 A | | 10/1996 | Sauer et al. | 606/176 |
| 5,669,927 A | | 9/1997 | Boebel et al. | 606/180 |
| 5,817,034 A | * | 10/1998 | Milliman et al. | 600/566 |
| 5,843,017 A | * | 12/1998 | Yoon | 604/22 |
| 6,015,017 A | * | 1/2000 | Lauterwald | 173/48 |
| 6,032,673 A | | 3/2000 | Savage et al. | 128/898 |
| 6,039,748 A | | 3/2000 | Savage et al. | 606/180 |
| 6,361,504 B1 | | 3/2002 | Shin | 600/562 |
| 6,391,043 B1 | | 5/2002 | Moll et al. | 606/174 |
| 6,398,741 B2 | | 6/2002 | Niizeki et al. | 600/566 |
| 6,419,684 B1 | | 7/2002 | Heisler et al. | 606/170 |
| 6,428,539 B1 | | 8/2002 | Baxter et al. | 606/49 |
| 6,468,228 B1 | | 10/2002 | Topel et al. | 600/567 |
| 6,554,778 B1 | | 4/2003 | Fleming, III | 600/567 |
| 6,572,632 B2 | | 6/2003 | Zisterer et al. | 606/170 |
| 6,589,240 B2 | | 7/2003 | Hinchliffe | 606/47 |
| 6,685,724 B1 | | 2/2004 | Haluck | |
| 6,689,140 B2 | * | 2/2004 | Cohen | 606/103 |
| 6,702,813 B1 | | 3/2004 | Baxter et al. | 606/49 |
| 6,923,783 B2 | * | 8/2005 | Pasqualucci | 604/27 |
| 7,033,357 B2 | | 4/2006 | Baxter et al. | 606/49 |
| 2002/0035372 A1 | * | 3/2002 | Zisterer et al. | 606/180 |
| 2003/0204188 A1 | * | 10/2003 | Morrison et al. | 606/45 |
| 2003/0225344 A1 | | 12/2003 | Miller | |
| 2004/0102772 A1 | | 5/2004 | Baxter et al. | 606/45 |
| 2006/0189920 A1 | * | 8/2006 | Seeh | 604/22 |

FOREIGN PATENT DOCUMENTS

| | | |
|---|---|---|
| EP | 0 621 008 A | 10/1994 |
| WO | WO94/02075 | 2/1994 |
| WO | WO 99/07295 A | 2/1999 |
| WO | WO99/29238 | 6/1999 |

OTHER PUBLICATIONS

International Search Report dated Jul. 31, 2007.

* cited by examiner

*Primary Examiner* — Ryan Severson
*Assistant Examiner* — Ashley Cronin

(57) ABSTRACT

A surgical morcellator includes a trocar body portion and a handle portion detachably mounted to the trocar body portion. The trocar body portion is relatively lightweight and may be used separately from the handle portion with other laparoscopic instruments while morcellation is not required during the surgical procedure.

15 Claims, 23 Drawing Sheets

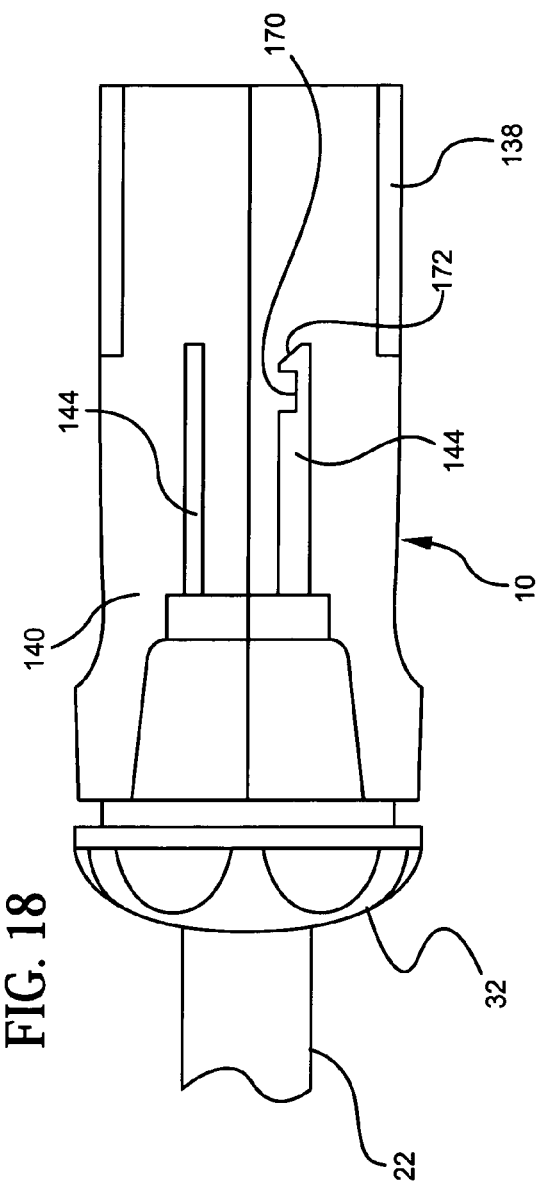
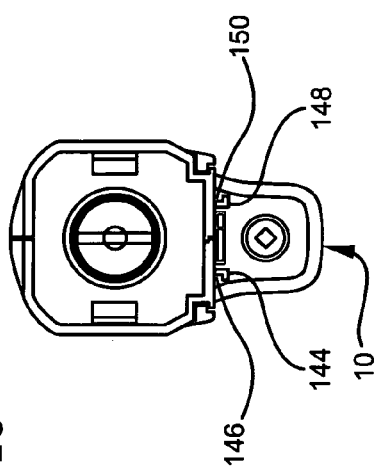
FIG. 18
FIG. 19

MORCELLATOR WITH DETACHABLE HANDLE

BACKGROUND OF THE INVENTION

1. Field of the Invention

The present invention relates generally to surgical devices and methods, and more particularly to a laparoscopic morcellator having a detachable handle and various other improved features.

2. Description of the Prior Art

Minimally invasive surgical procedures, such as laparoscopic procedures, have become very common. These procedures typically involve one or more small incisions that provide access to the relevant internal organ or tissue. A trocar, cannula or the like is placed into each incision, and all surgical steps are subsequently performed with instruments passed through or into the trocar(s).

Many times it is desirable to remove relatively large masses of tissue, for example a uterine fibroid, which can be difficult and time consuming given the diameter of the trocar. To this end, laparoscopic morcellators have been developed to assist in severing the tissue mass into pieces that can readily be removed through the trocar. An example of one such a morcellator is described in detail in U.S. Pat. No. 6,039,748, which is incorporated herein by reference in its entirety.

Known morcellators typically include a rotating tube having a sharp distal cutting edge, which rotates within an outer stationary tube. The morcellator is inserted through a cannula or trocar, or more commonly directly through the incision. A grasping instrument (i.e., tenaculum) is inserted through the inner rotating tube. Using the tenaculum, the surgeon pulls the tissue to be severed up into the tube so that the rotating edge of the inner tube severs the grasped portion of tissue. By repeating the grasping and severing procedure, the surgeon can remove the large tissue mass in increments.

Another technique surgeons have developed to improve the speed of tissue removal using a morcellator is known as "orange peeling." In orange peeling, the cylindrical blade of the morcellator is held on a plane with the outside of the organ or tissue being removed in such a way as to allow the organ or tissue to be rotated. This allows a longer strip to be removed as opposed to the "coring" technique described above, which limits the length of the strip removed to the thickness of the organ. Orange peeling requires skill of the surgeon holding the morcellator as well as skill of the assistant that is passing tissue to the morcellator with a second grasper in the cavity. The skill required is in keeping the blade at the surface of the tissue without either allowing the blade to dive in, or "core", and at the same time not leaving the surface so much that the tissue strip becomes thin or breaks. Orange peeling is better from a safety standpoint as well, as the blade remains visible at all times to the user. Thus, it would be desirable to provide a morcellator having improved feature(s) that facilitate the ability of the surgeon to use the orange peeling technique.

Another difficulty sometimes encountered with known morcellators is that during use, whether by coring or orange peeling, the amount of tissue being withdrawn can cause friction within the inner rotating tube or to the seal system during removal. The larger the tissue sections or strips, the more exaggerated this problem becomes. It would further be desirable to provide a morcellator that lowers such withdrawal forces.

In addition to friction encountered during tissue removal, manipulation of the grasping instrument within the rotating inner tube can interfere with the blade rotation and tends to lead to dulling of the blade with known morcellators, since the sharp edge is positioned on the inner most point on the circumference of the inner tube. It would also be desirable to provide a morcellator that provides increased protection against such interference and blade dulling.

Finally, as indicated above, morcellators are typically inserted through a cannula, or more commonly directly through the incision. When inserted directly into the incision the existing trocar must first be removed. Following morcellation, if any other procedures or tasks are to be performed within the cavity, the morcellator must be removed before any other laparoscopic instrument can be inserted through that same portal. Removal and reinsertion of trocars and laparoscopic instruments during a given procedure is awkward and time consuming, and creates additional trauma at the site. It is further desirable to provide a morcellator that will greatly reduce the need for such exchanges.

OBJECTS AND SUMMARY OF THE INVENTION

It is an object of the present invention to provide a surgical morcellator having a detachable handle.

It is another object of the present invention to provide a surgical morcellator having a separable trocar body portion that may serve as a trocar for other surgical instruments.

It still another object of the present invention to provide a surgical morcellator having a detachable handle and a trocar body portion that eliminates the need for separate devices (trocar and morcellator) during a surgical procedure.

It is a further object of the present invention to provide a surgical morcellator that reduces trauma to the patient and requires fewer instruments during a surgical procedure.

It is yet a further object of the present invention to provide a surgical morcellator that maintains pneumoperitineum during a surgical procedure.

It is still a further object of the present invention to provide a surgical morcellator that minimizes or eliminates negative pressure within a trocar body portion of the morcellator when withdrawing tissue or instruments therethrough.

It is another object of the present invention to provide a surgical morcellator that may be used with many other surgical instruments.

It is yet another object of the present invention to provide a surgical morcellator having a detachable handle and an interlock that prevents the sharpened edge of the morcellator cutting blade from being exposed when the handle is detached therefrom.

It is a still a further object of the present invention to provide a surgical morcellator having a low drag seal system.

It is yet another object of the present invention to provide a surgical morcellator that allows a surgical procedure to be performed with greater speed, with less trauma to the incision site through fewer reinsertions of surgical instruments, and with a reduced need for instrumentation and a reduced cost for each surgical procedure.

In accordance with one form of the present invention, a surgical morcellator includes a trocar body portion and a handle portion detachably mounted to the trocar body portion. The morcellator further preferably includes a handle portion detachment mechanism that is situated on the trocar body portion and the handle portion and which detachably mounts the handle portion to the trocar body portion. In one form of the present invention, the handle portion detachment mechanism includes at least one first member situated on the handle portion and at least one second member situated on the trocar body portion. The at least one first member and the at least one second member cooperatively engage one another to detachably secure the handle portion on the trocar body portion. A push button actuator is provided for disengaging the handle portion from the trocar body portion of the morcellator. The push button actuator is preferably mounted on the handle portion and includes a push button projection that is exposed through an opening in the housing of the handle portion, and a tab that is received by a notch formed in the at least one second member situated on the trocar body portion. The tab is selectively received by the notch to secure the handle portion to the trocar body portion, and is unseated from the notch when the push button projection is pressed by the surgeon to allow the handle portion to be detached from the trocar body portion.

The trocar body portion is relatively lightweight and may be used separately from the handle portion and serve as a trocar for other laparoscopic instruments while morcellation is not required during the surgical procedure.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 18 is a bottom view of the trocar body portion of the morcellator of the present invention shown in FIG. 2.

FIG. 19 is a rear end view of the trocar body portion of the morcellator of the present invention shown in FIG. 2.

DETAILED DESCRIPTION OF THE PREFERRED EMBODIMENTS

Figure 1:
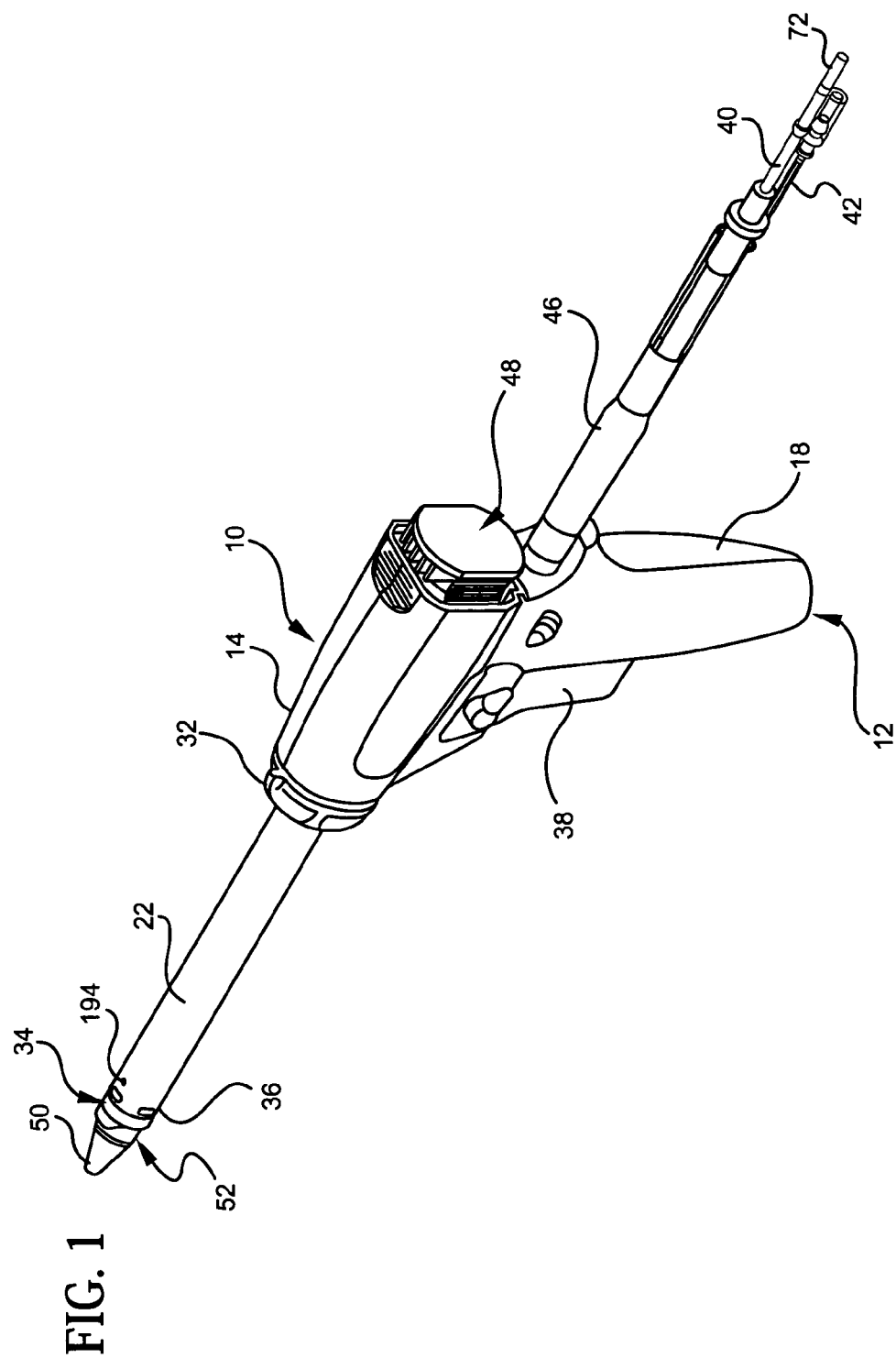
FIG. 1 is an isometric view of a surgical morcellator having a detachable handle portion constructed in accordance with one form of the present invention.
Figure 2:
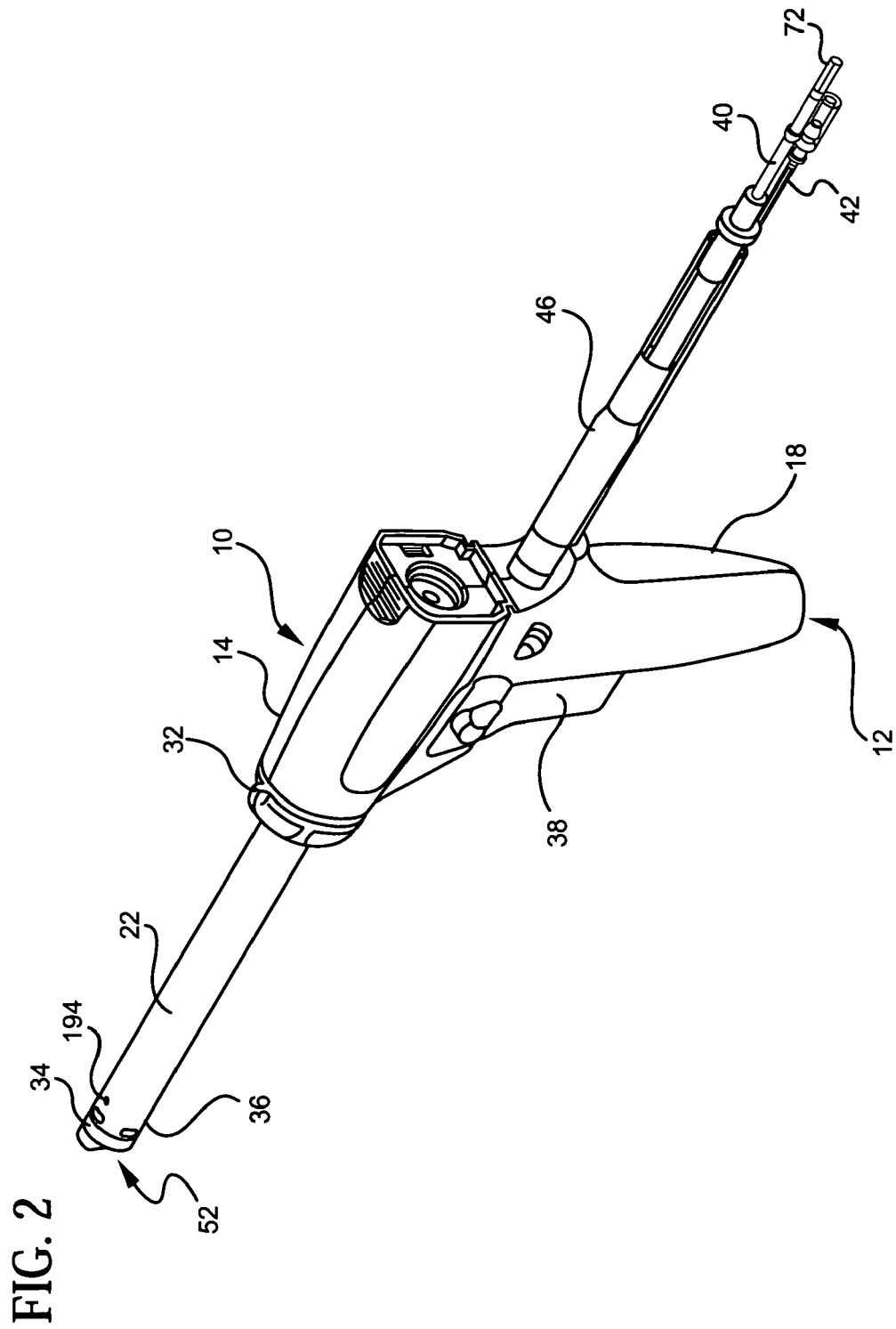
FIG. 2 is an isometric view of the morcellator shown in FIG. 1 with an entry protector member removed therefrom.
Figure 3:
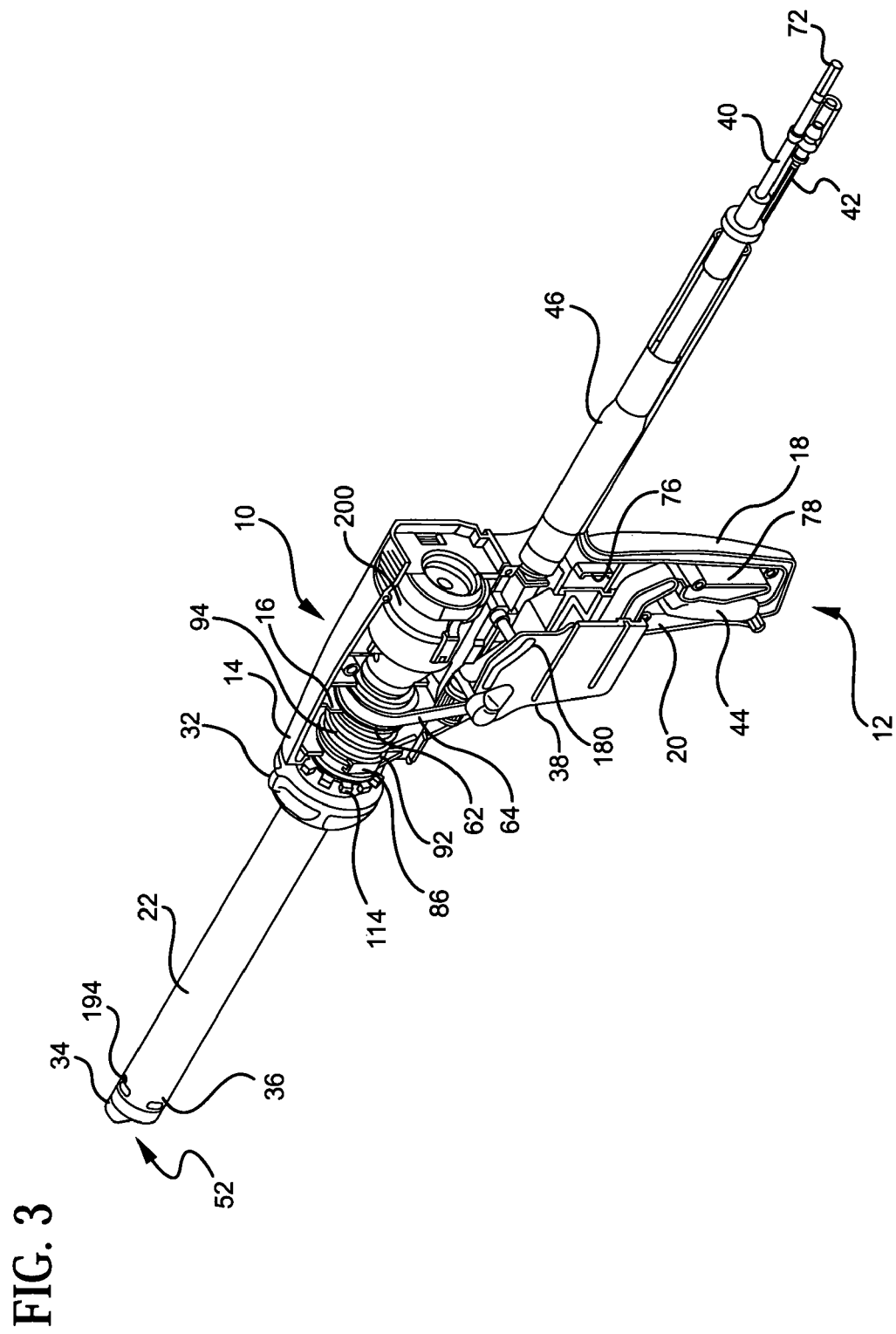
FIG. 3 is a isometric view of the morcellator of the present invention shown in FIG. 2 having the housing thereof partially broken away to view the internal components thereof.
Figure 4:
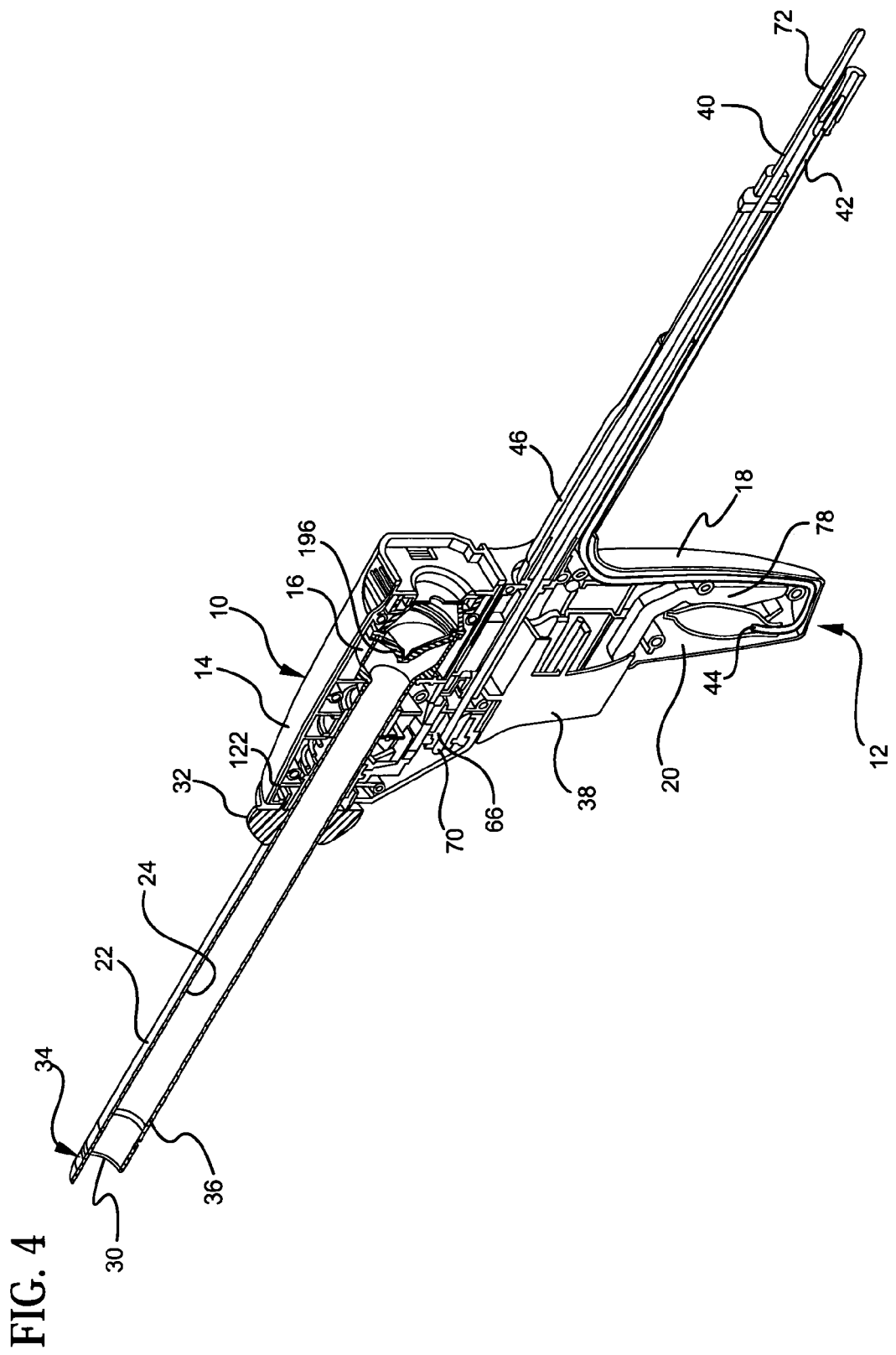
FIG. 4 is an isometric, cross-sectional view of the morcellator of the present invention shown in FIG. 2, illustrating various components thereof.
Figure 5:
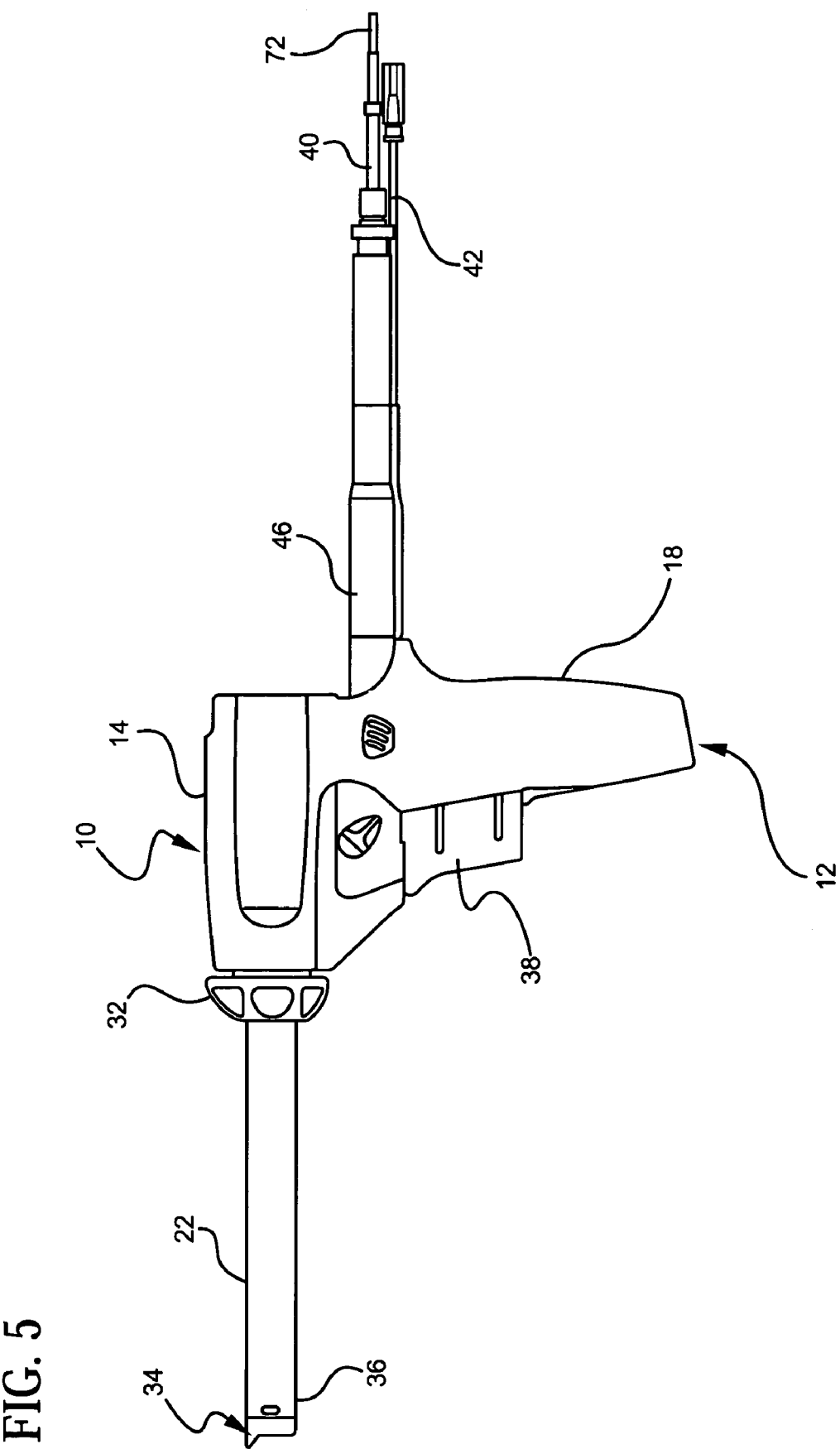
FIG. 5 is a side view of the morcellator of the present invention shown in FIG. 2.
Figure 6:
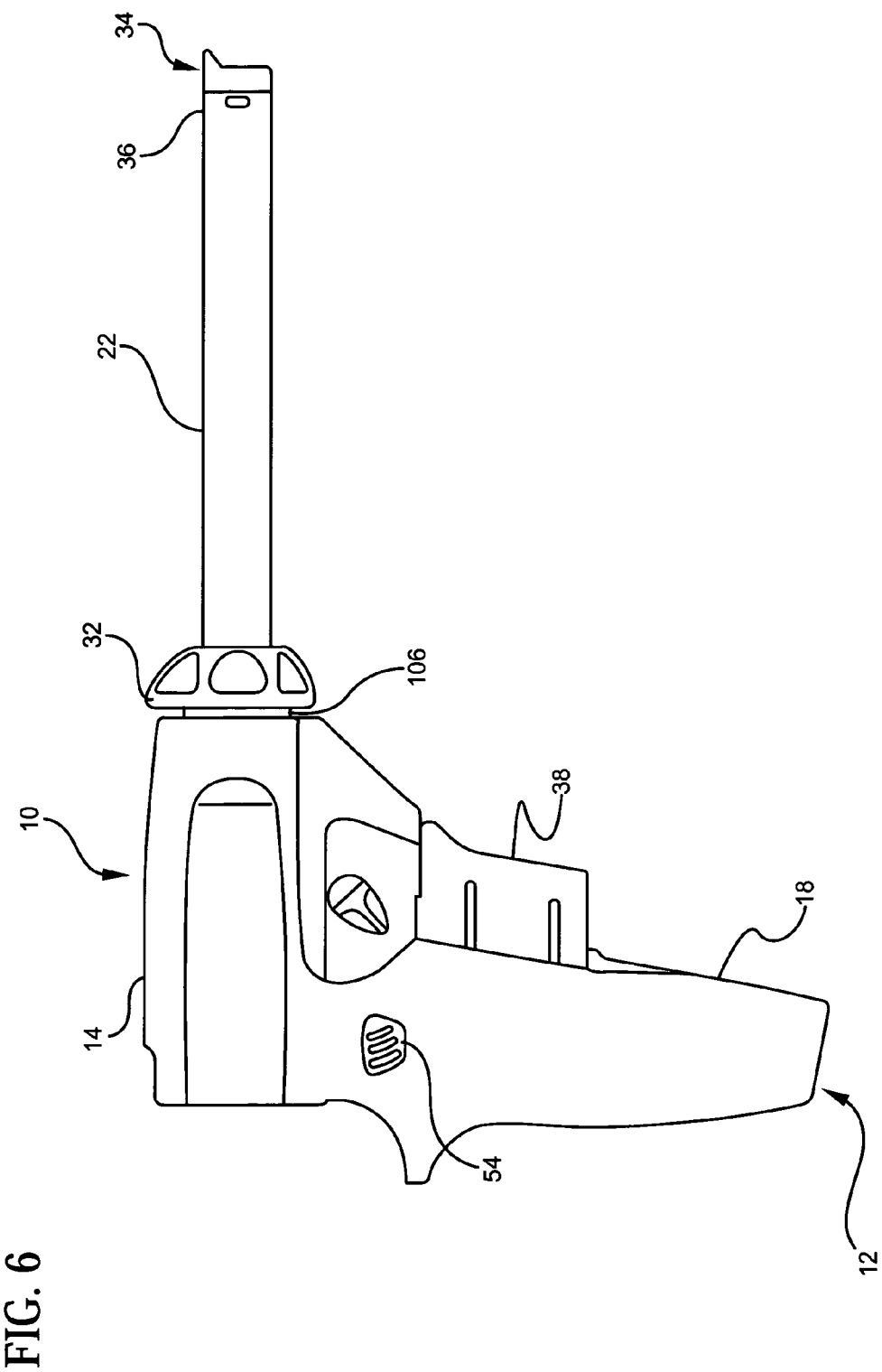
FIG. 6 is an opposite side view of the morcellator of the present invention shown in FIG. 5, with the drive cable being omitted therefrom, and illustrating the push button used for detaching the handle portion from the trocar body portion of the morcellator.
Figure 7:
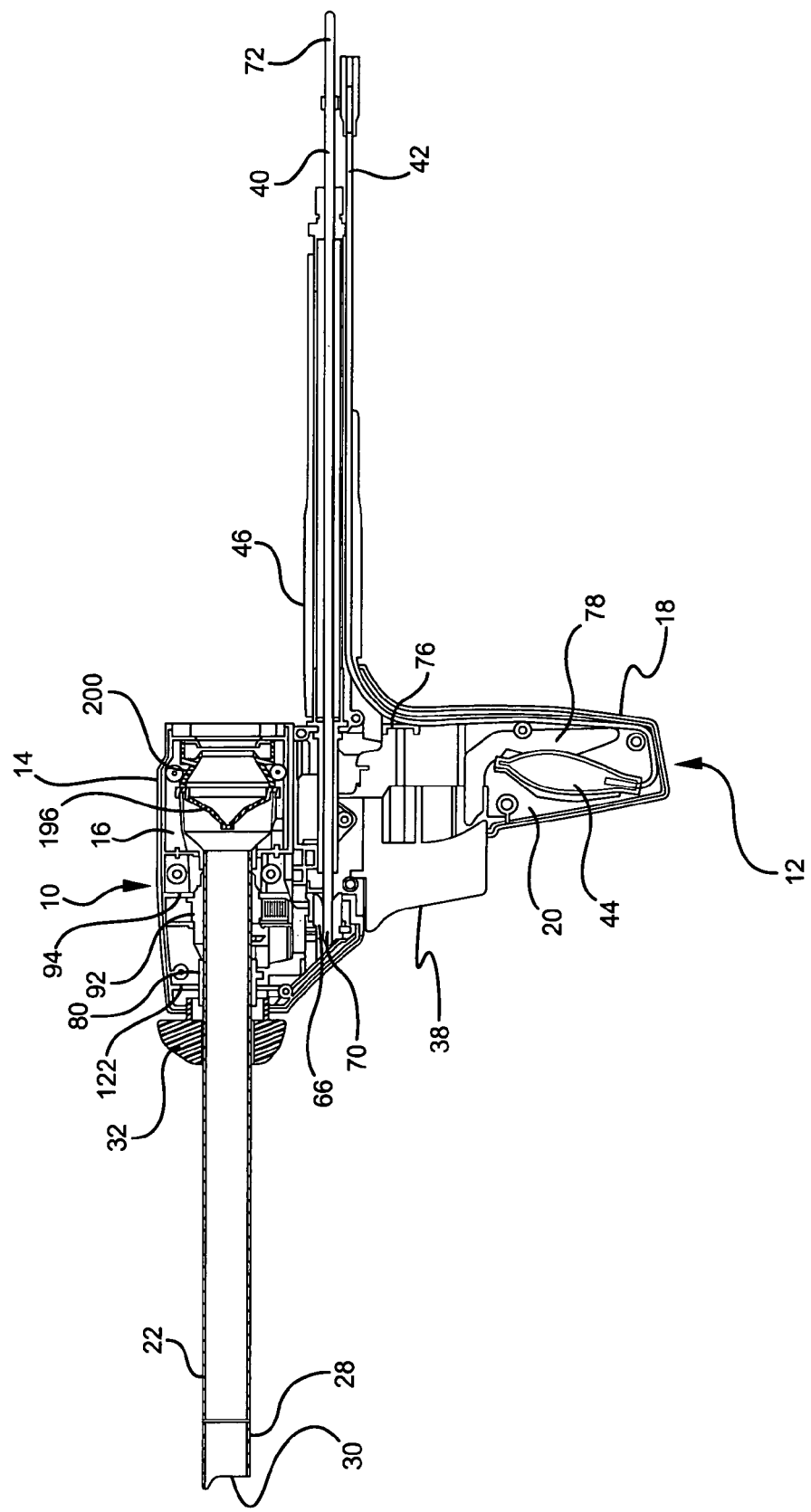
FIG. 7 is a partial cross-sectional view of the morcellator of the present invention shown in FIG. 5.
Figure 8:
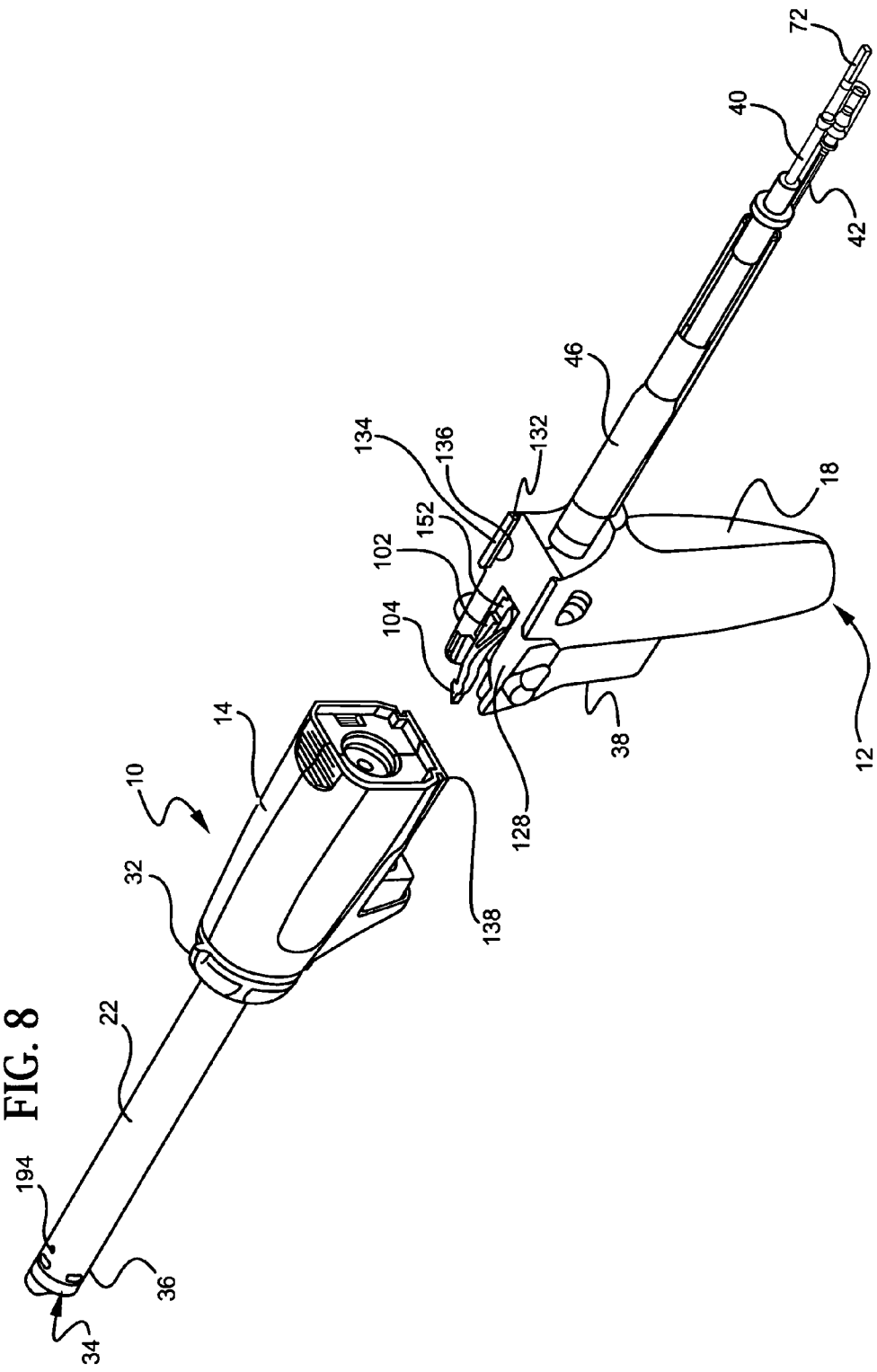
FIG. 8 is an isometric, partially exploded view of the morcellator of the present invention shown in FIG. 2.
Figure 9:
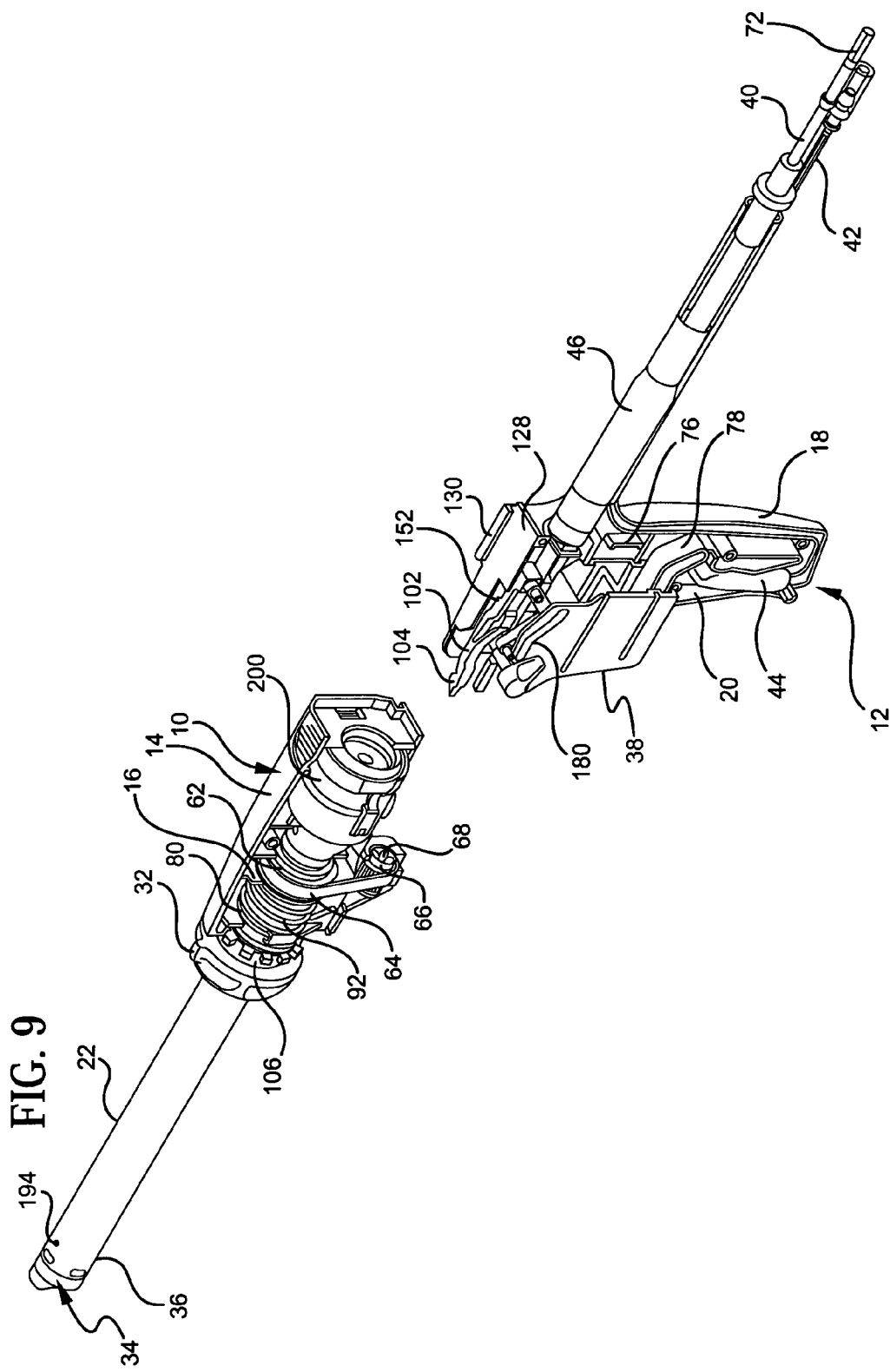
FIG. 9 is an isometric, partially exploded view of the morcellator of the present invention shown in FIG. 8 with the housing thereof partially broken away to view the internal components thereof.
Figure 10:
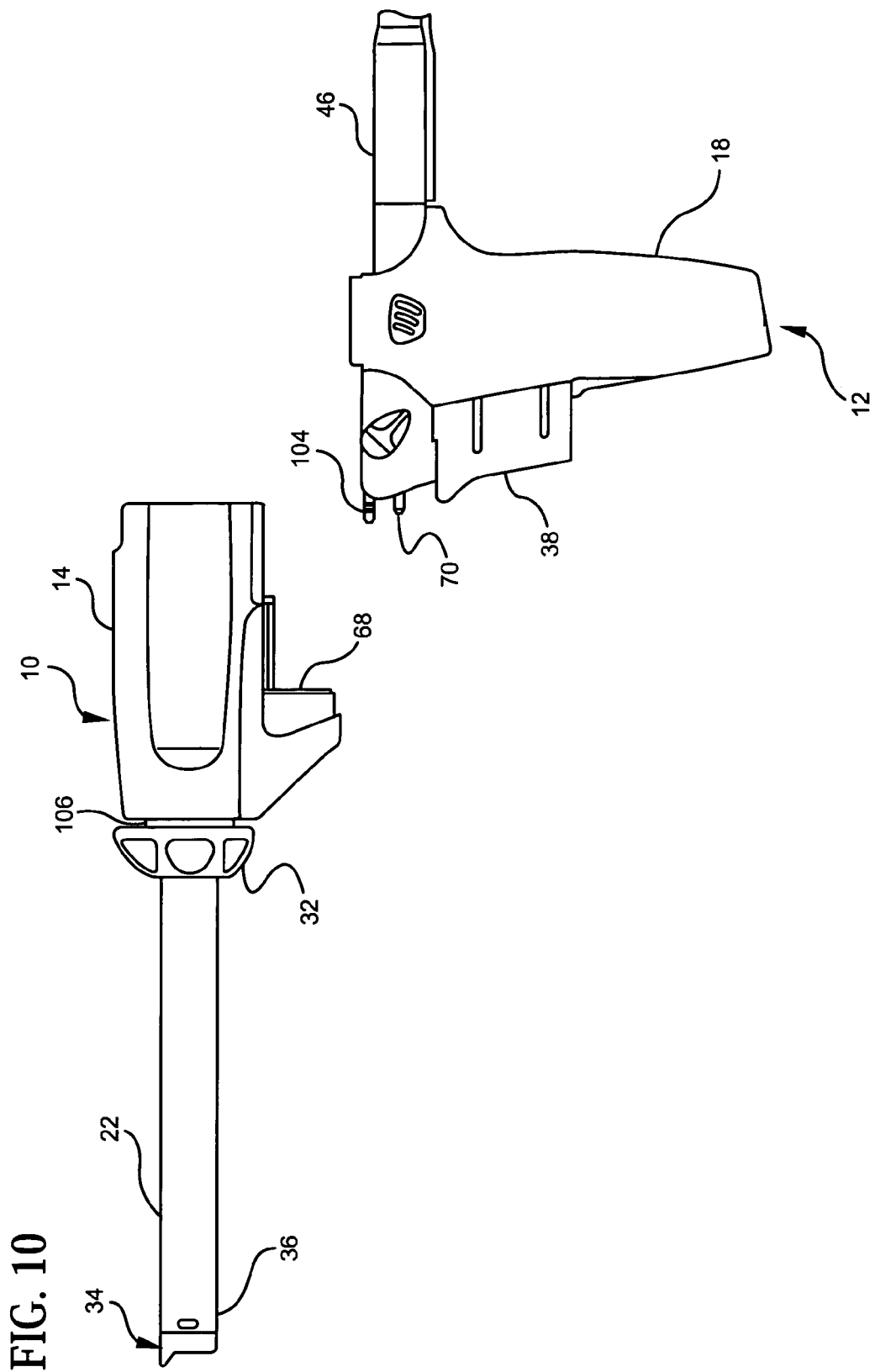
FIG. 10 is a side view of the main components of the morcellator of the present invention shown in FIG. 8.
Figure 11:
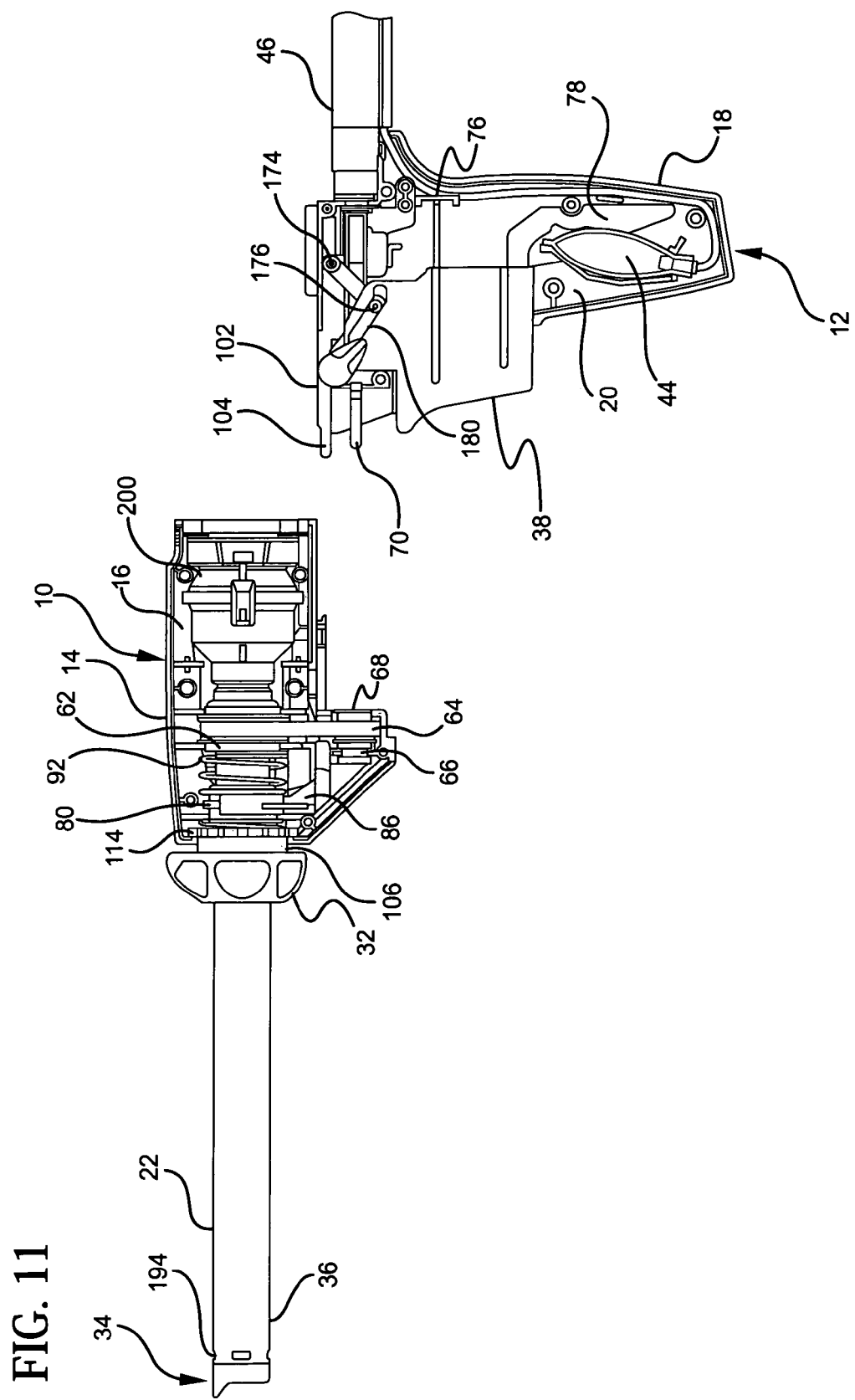
FIG. 11 is a combination side view and cross-sectional view of the main components of the morcellator of the present invention shown in FIG. 10.
Figure 12:
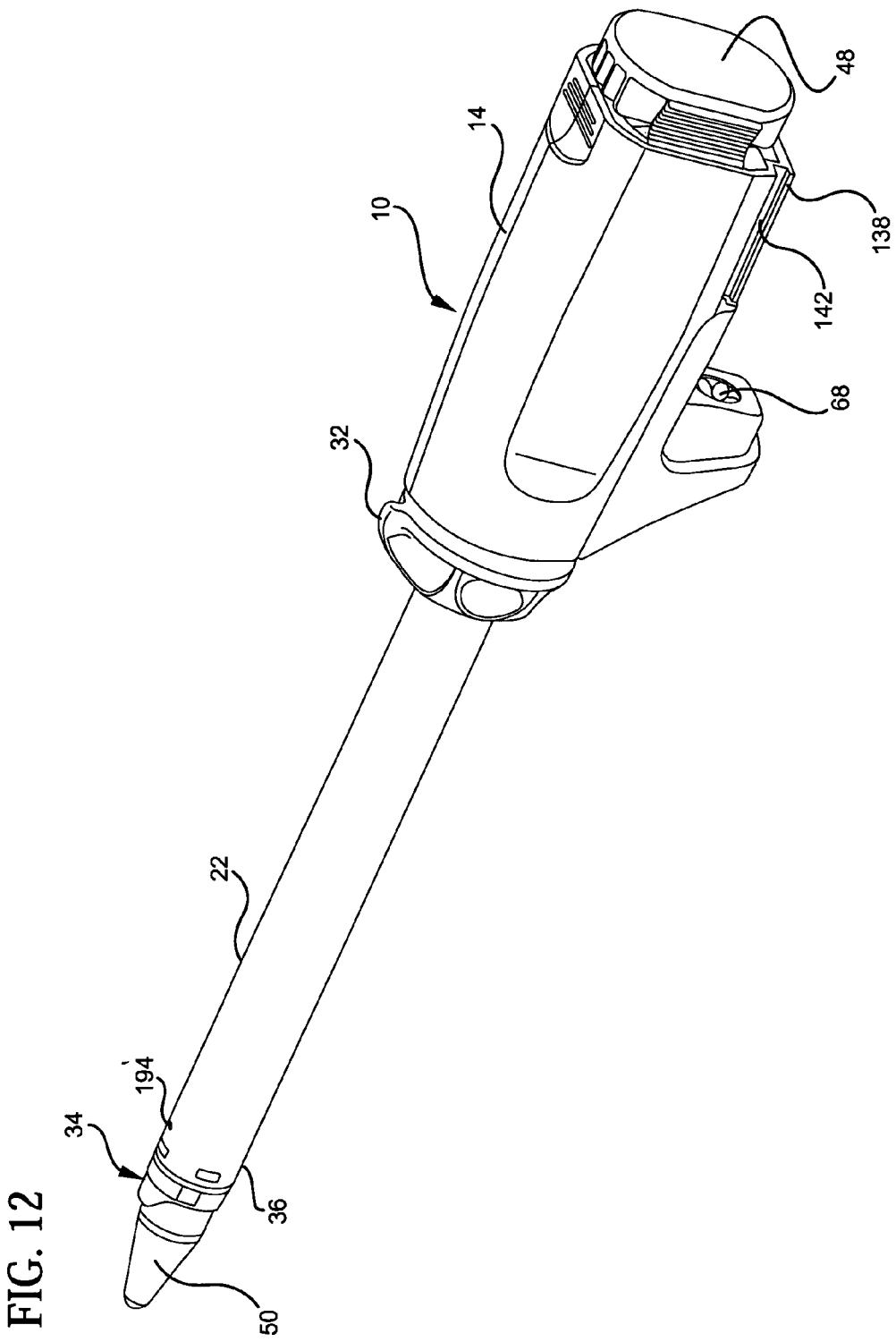
FIG. 12 is an isometric view of the trocar body portion of the morcellator of the present invention, and illustrating an entry protector member used therewith.
Figure 13:
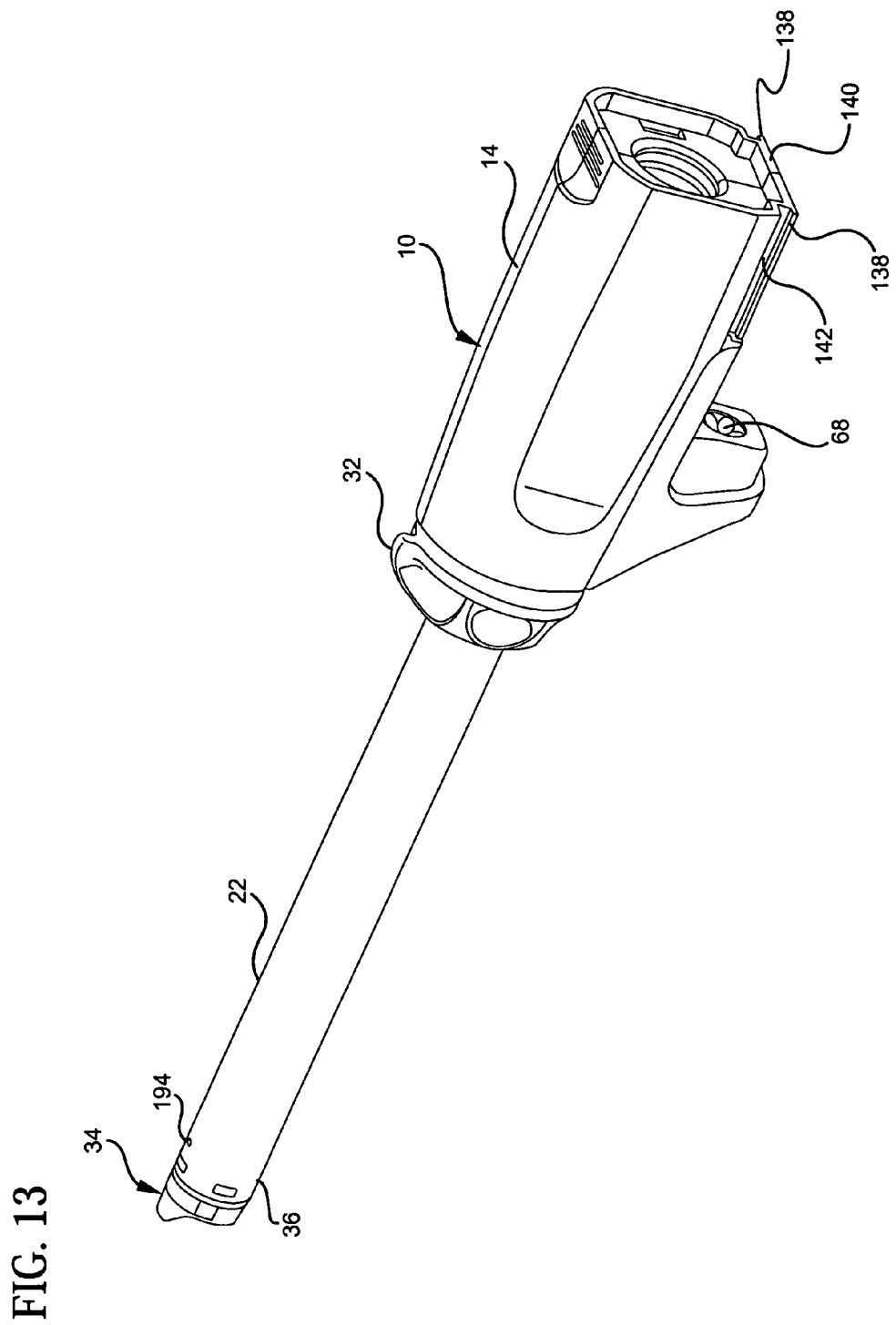
FIG. 13 is an isometric view of the trocar body portion of the morcellator of the present invention shown in FIG. 12, with the entry protector member being omitted.
Figure 14:
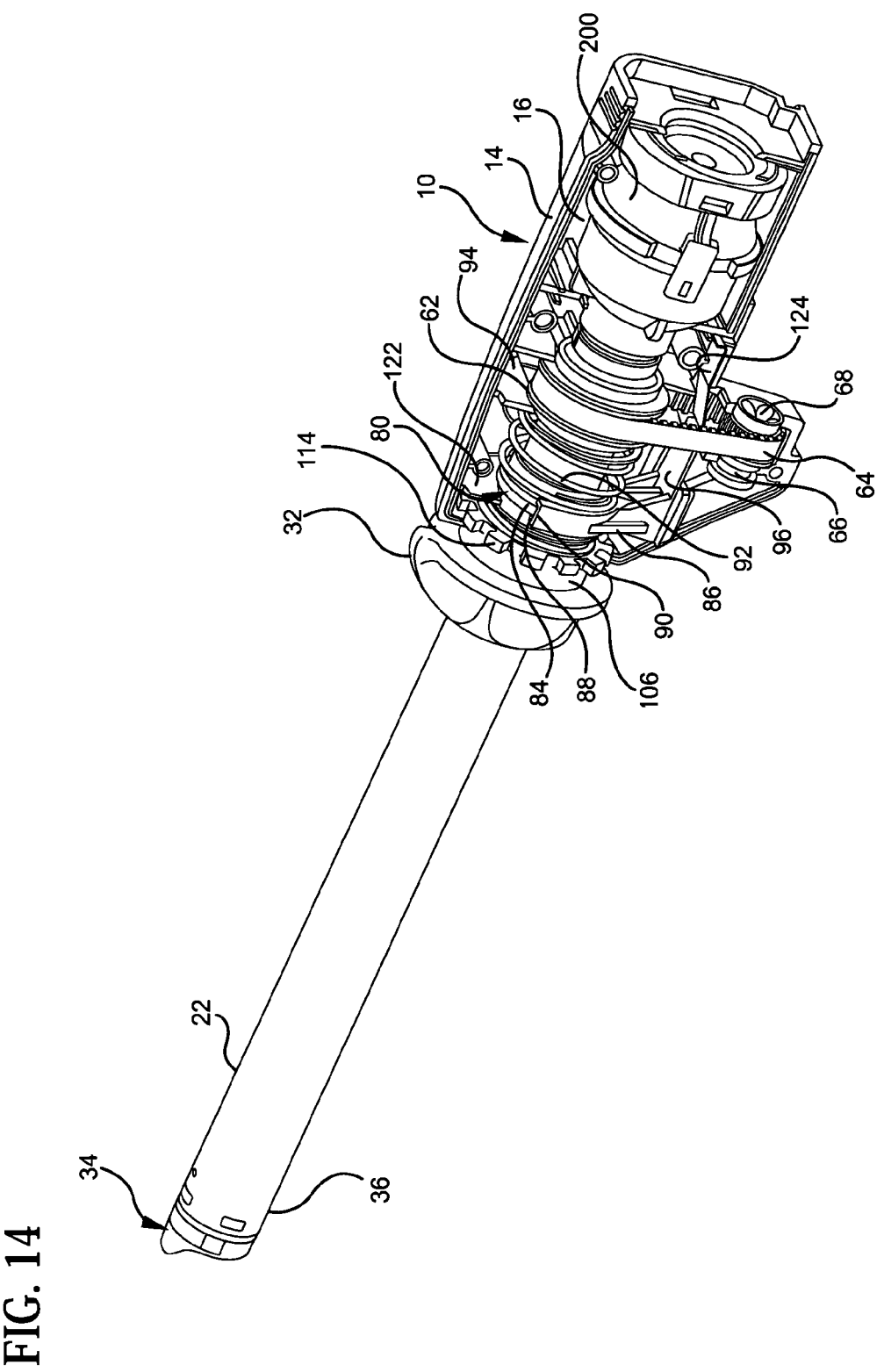
FIG. 14 is an isometric view of the trocar body portion of the morcellator of the present invention shown in FIG. 13, with the housing thereof partially broken away to view the internal components thereof.

The present invention is directed to a surgical morcellator having a detachable handle. Currently, physicians use trocars for laparoscopic surgery, especially during gynecologic surgery. For situations where large tissue specimens or anatomical bodies, such as organs, require removal, a morcellator, such as described in the aforementioned Savage, et al. patent, is placed through the trocar to debulk the tissue, or the trocar is removed and the morcellator is placed through the existing incision into the patient's body.

Currently used morcellators are too bulky and heavy and have attached power leads or lines which make it difficult for the surgeon to accurately manipulate the morcellator during surgery. Also, currently used morcellators frequently require that the trocar be removed from the incision and the morcellator introduced therethrough, which prolongs surgery and creates additional trauma at the surgical site. Furthermore, because a trocar is limited in diameter, devices such as morcellators which pass therethrough must have an effective diameter that is greatly reduced in order to be received by the trocar. Frequently, at the end of a surgical procedure, the morcellator is removed and the trocar is reinserted to perform the final steps of the procedure.

The advantage of the morcellator of the present invention with its detachable handle is that it eliminates the need to have two separate devices (trocar and morcellator) by providing a combined device that allows the entire procedure to be conducted through the morcellator's trocar's aperture. In order to allow the entire surgical procedure to take place, a detachable handle containing the morcellator controls and power source can be removed to leave only the streamlined effective trocar body portion in place at the surgical site for the majority of the procedure. The handle can be clipped back onto the trocar body portion to enable morcellation as needed without requiring the surgeon to remove the trocar body portion from the patient's incision. The morcellator with its detachable handle also maintains pneumoperitinum during the surgical procedure.

One of the unique features of the morcellator of the present invention is that the handle with the power cable attached thereto may be removed to allow the lightweight, smaller trocar body portion of the morcellator to remain in the cavity of the patient and serve as an entry port while morcellation is not required. Because the trocar body portion of the morcellator is relatively lightweight, the surgeon may manipulate the trocar body portion with accuracy during surgery, and yet provide morcellation capability as required, and without requiring the insertion of a second device or switching from one device to another device at the incision site.

Now, initially referring to FIGS. 1-8 of the drawings, a surgical morcellator constructed in accordance with one form of the present invention generally includes a trocar body portion 10 and a handle portion 12 detachably mounted on the trocar body portion 10. The trocar body portion 10 includes a housing 14 preferably formed with mating half sections, which housing defines an internal cavity 16 for situating therein the various operating components of the trocar body portion 10. Similarly, the handle portion 12 includes a housing 18, also preferably formed with mating half sections, which housing defines an internal cavity 20 for situating therein the components for operating the morcellator. The various internal components of the trocar body portion 10 and the handle portion 12 are illustrated in the cross-sectional views of such portions shown in FIGS. 3, 4 and 7, as well as in other figures, and certain of these components relating to the handle detachment mechanism and other features of the morcellator will be discussed in greater detail.

Figure 15:
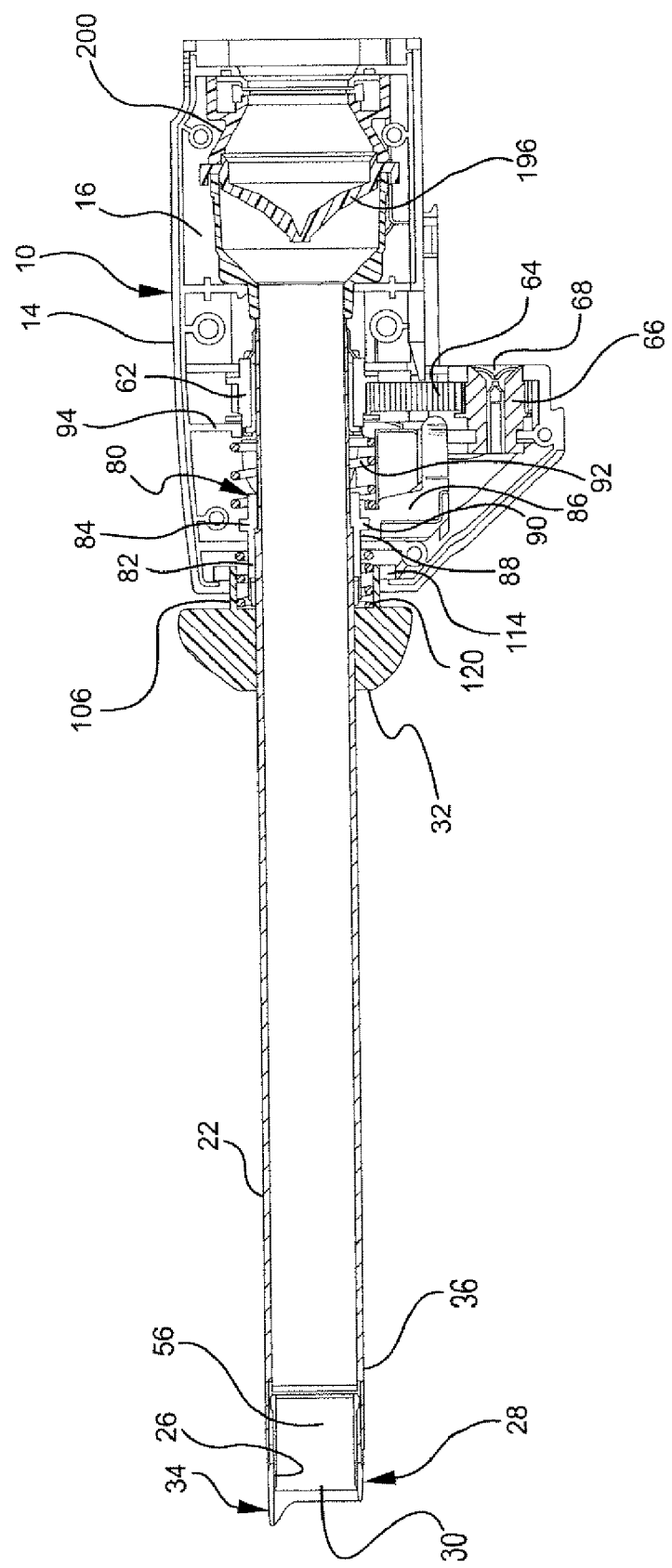
FIG. 15 is a partial cross-sectional view of the trocar body portion of the morcellator of the present invention shown in FIG. 14.
Figure 16:
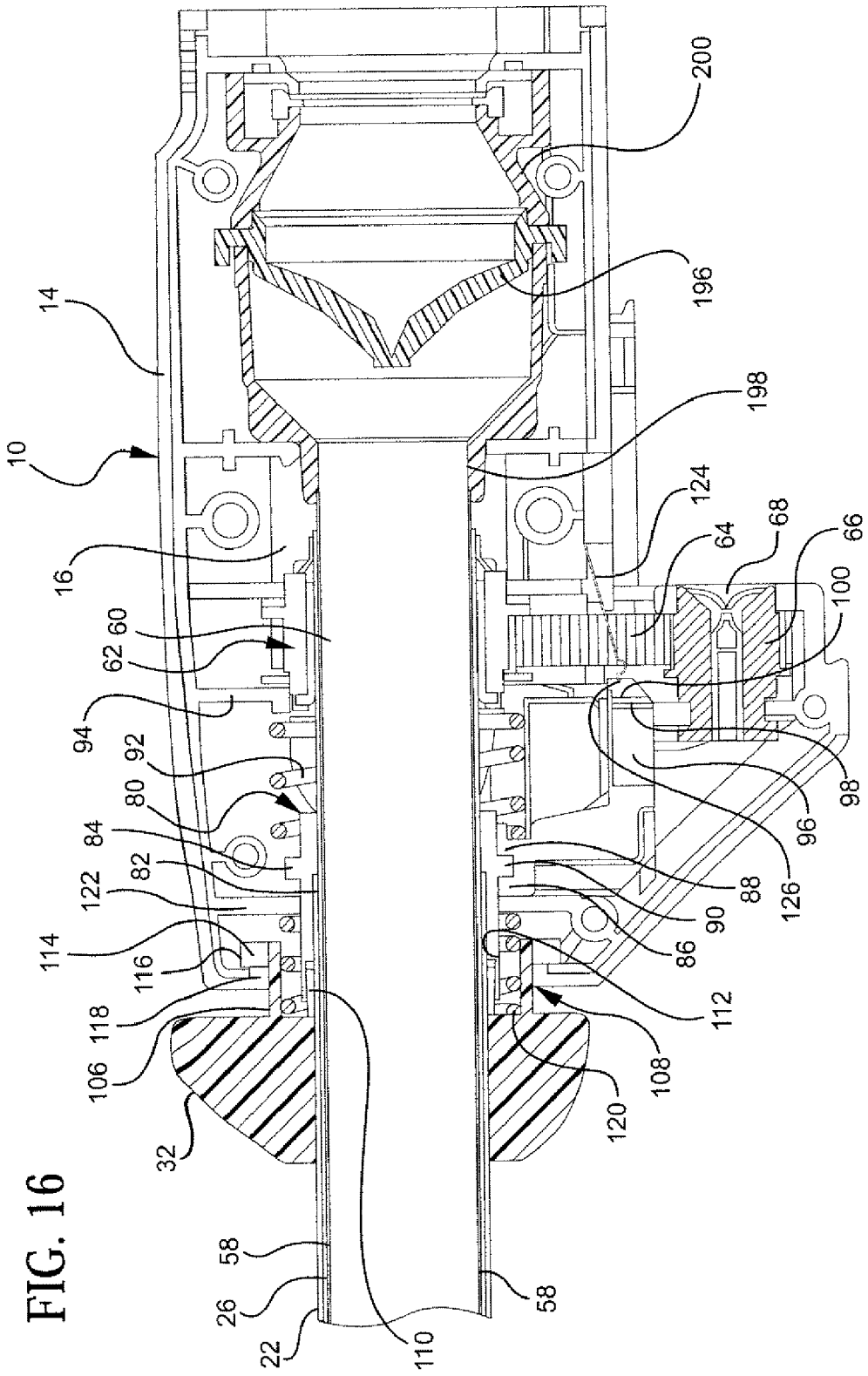
FIG. 16 is a detailed, partial cross-sectional view of the trocar body portion of the morcellator of the present invention shown in FIG. 15.
Figure 17:
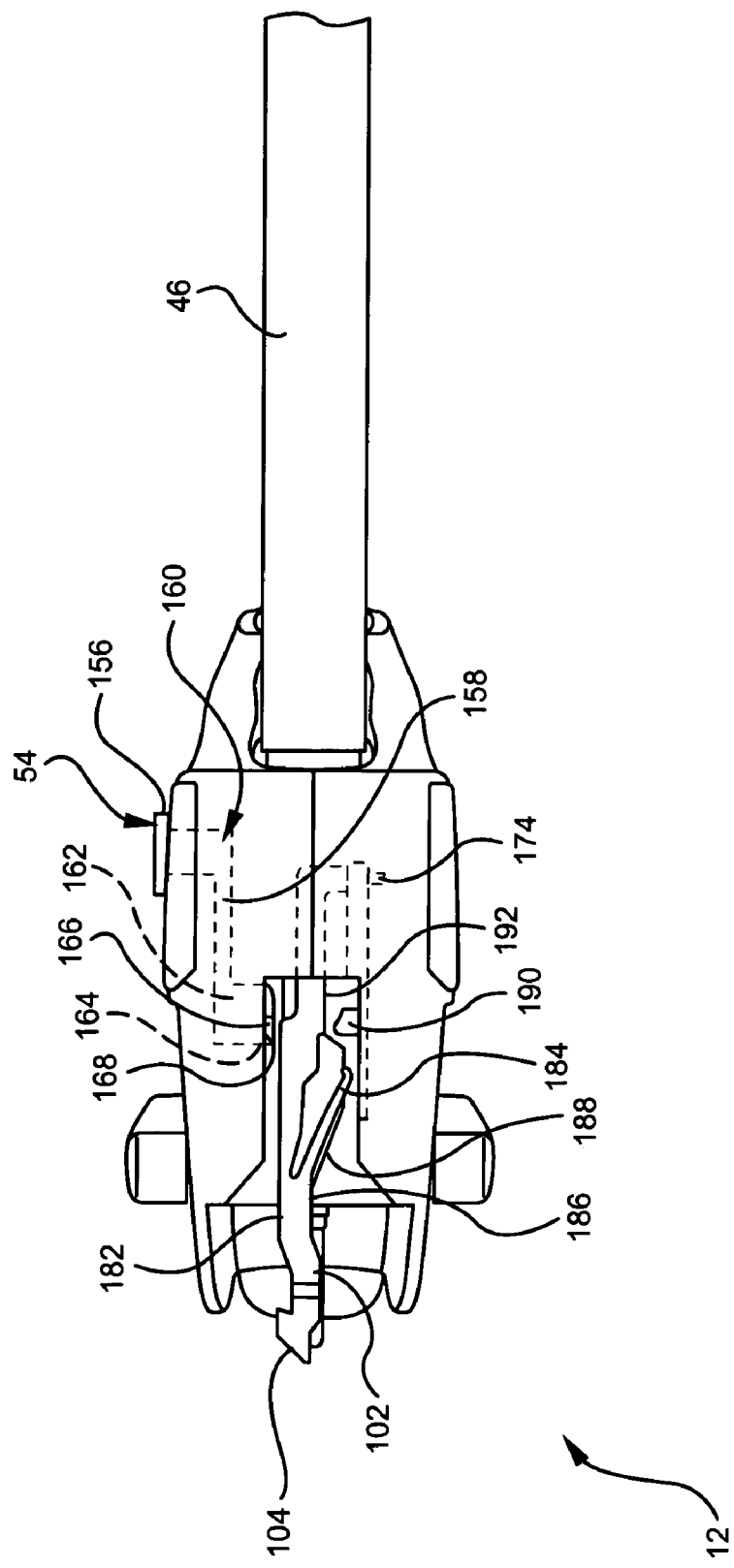
FIG. 17 is a top view of the handle portion of the morcellator of the present invention shown in FIG. 2.
Figure 20:
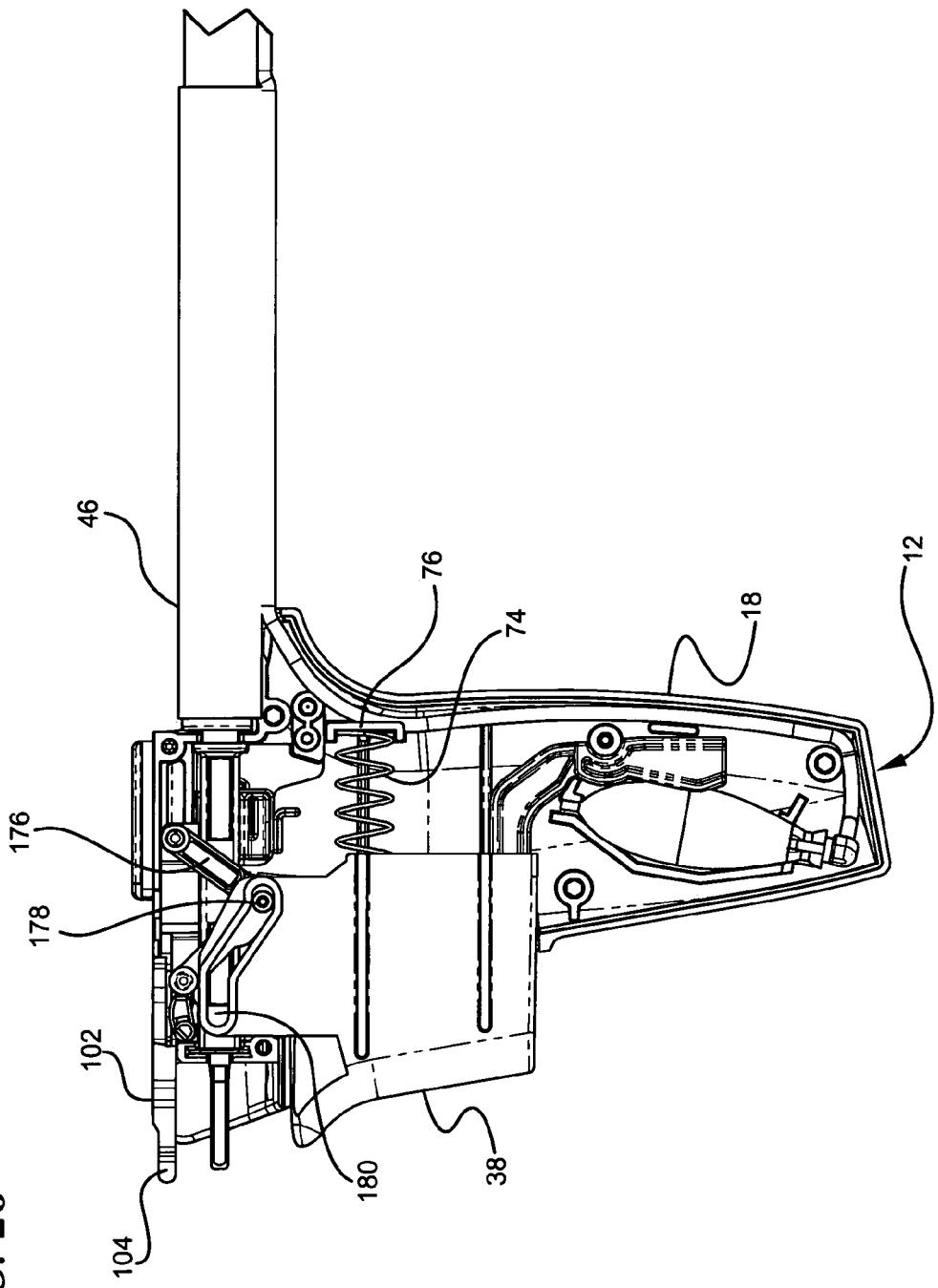
FIG. 20 is a cross-sectional view of the handle portion of the morcellator of the present invention shown in FIG. 2.
Figure 21:
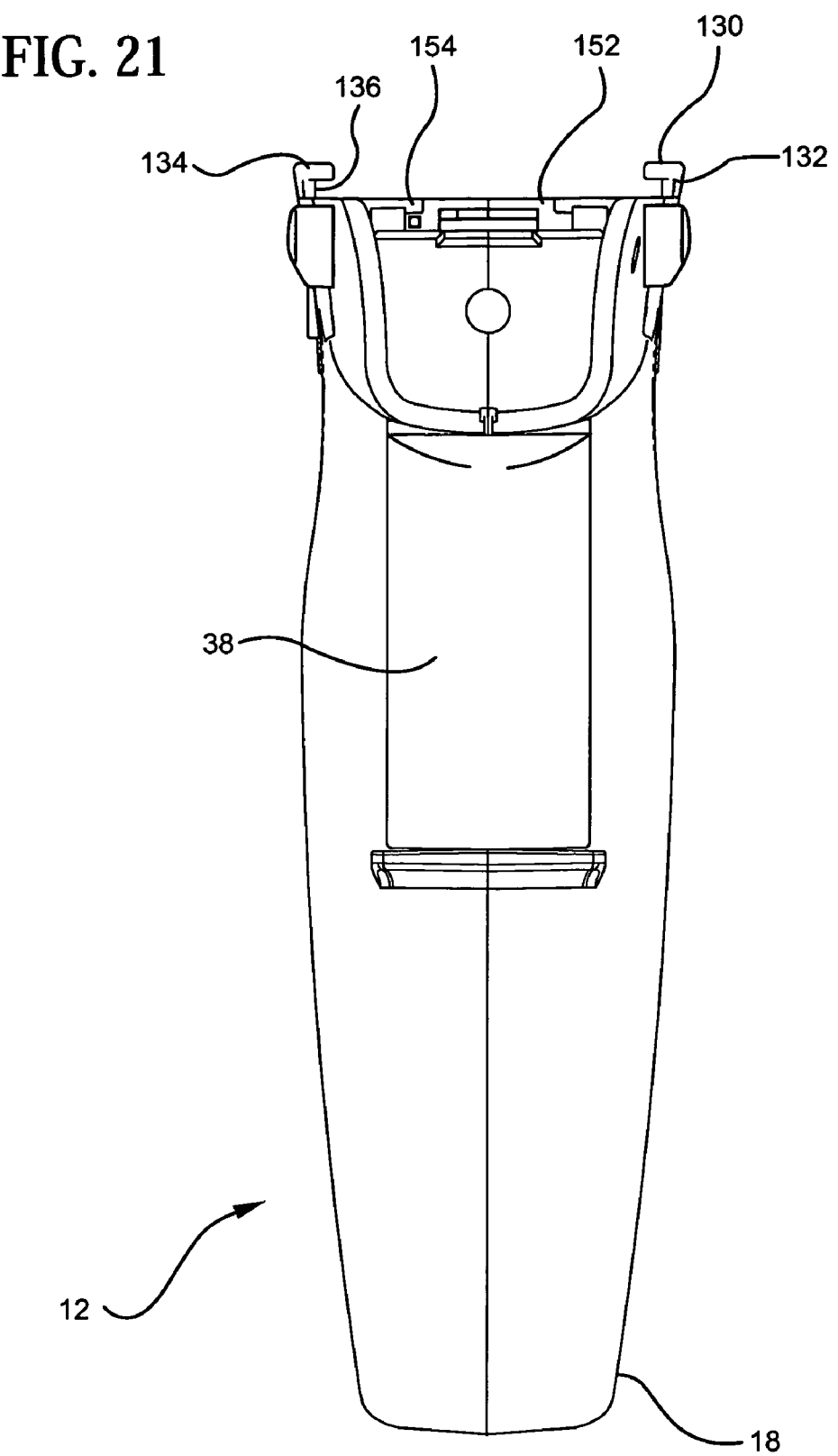
FIG. 21 is a front view of the handle portion of the morcellator of the present invention shown in FIG. 2.
Figure 22:
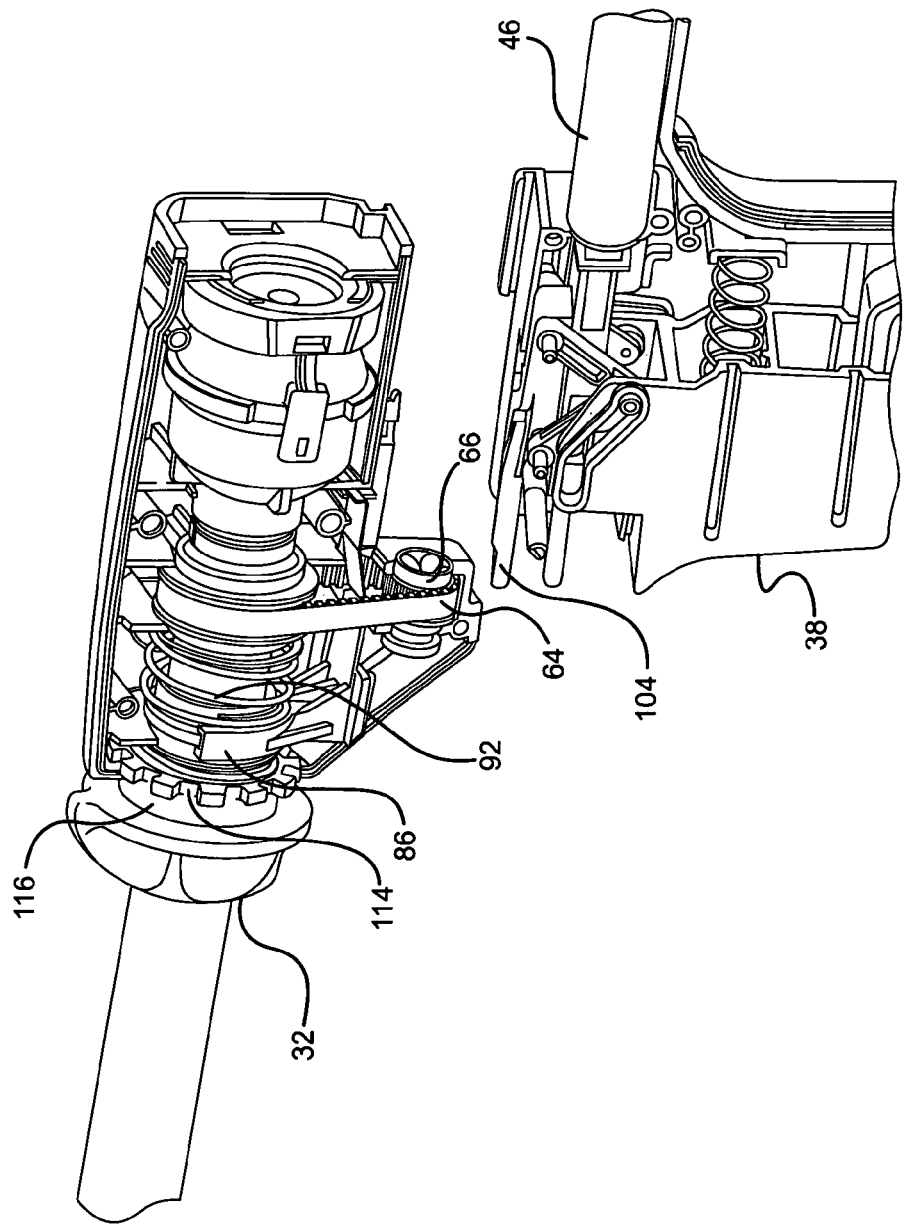
FIG. 22 is an isometric view of portions of the trocar body portion and handle portion of the morcellator of the present invention, with the housings thereof partially broken away to view the internal components thereof.
Figure 23:
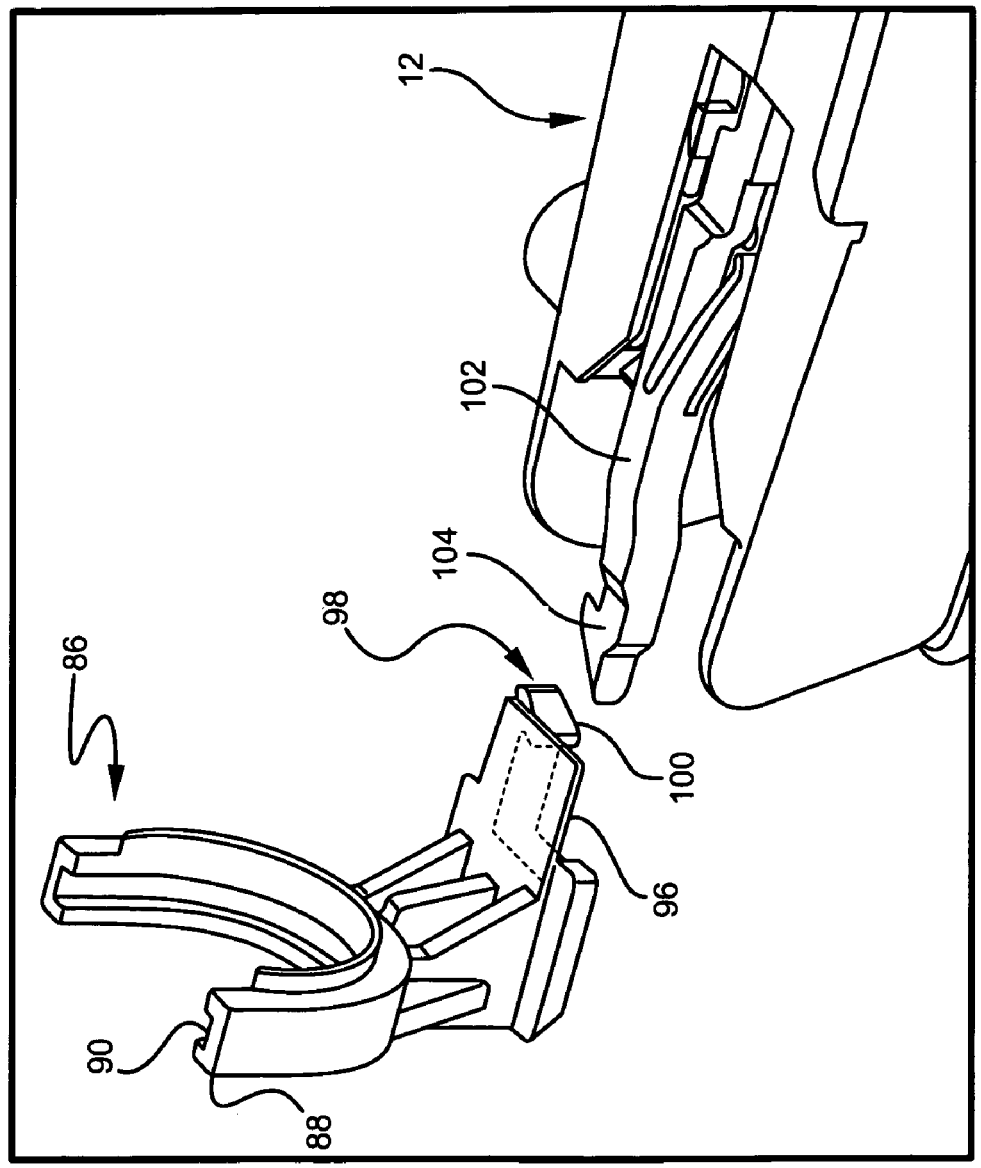
FIG. 23 is an exploded isometric view of components of the trocar body portion and handle portion of the morcellator of the present invention, illustrating the cooperation between the components that allow the handle portion to be detached from the trocar body portion.
Figure 24:
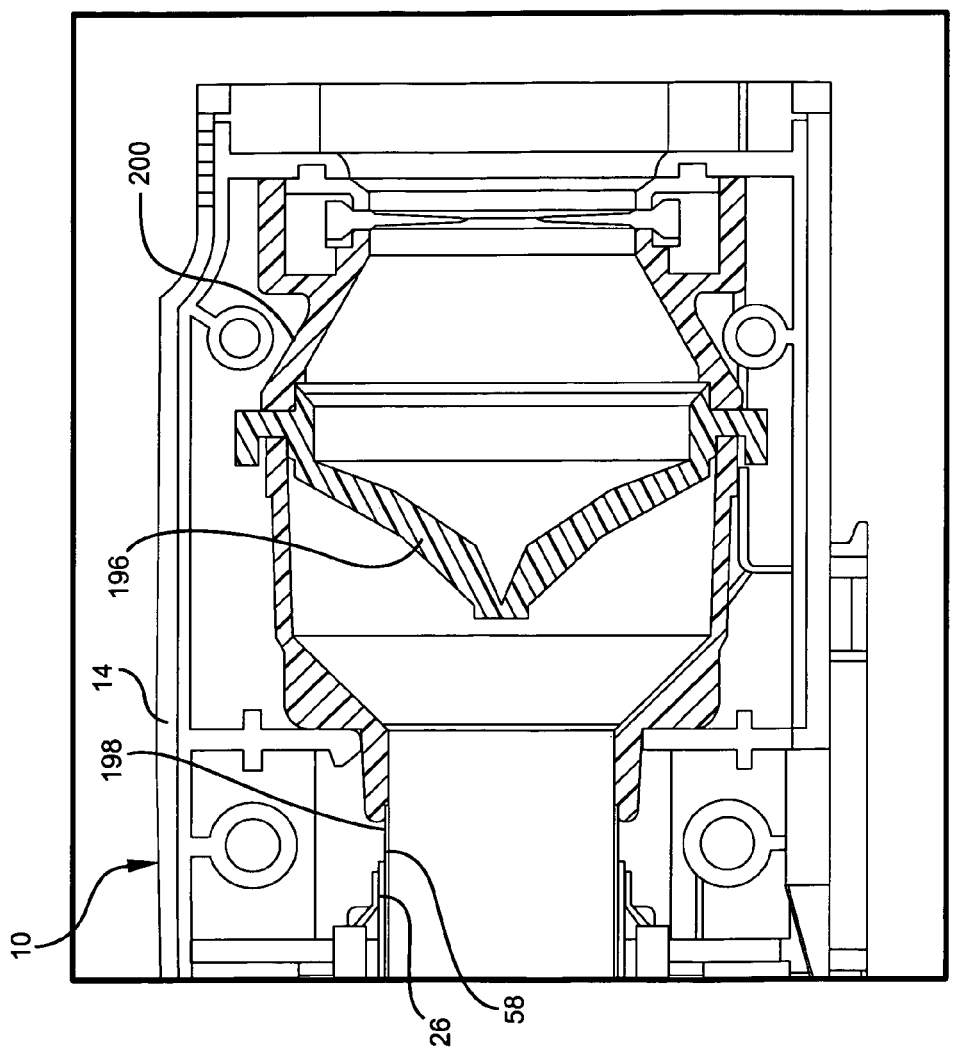
FIG. 24 is an enlarged cross-sectional view of a portion of the trocar body portion of the morcellator of the present invention shown in FIG. 2.

As can be seen from FIGS. 1-8, the trocar body portion includes an outer sleeve 22 formed as an elongated tubular member and which defines a bore 24 extending axially along the length thereof. A cutting blade 26 (see FIG. 15), also in the form of a tubular member, is situated within the bore 24 of the outer sleeve 22 and rotates therein. The distal end of the cutting blade 28 is formed with a sharpened edge 30 that is covered and uncovered by the outer sleeve 22. A knob 32 graspable by the surgeon is operatively coupled to the outer sleeve 22 in order to selectively position an anti-coring device 34 mounted on the distal end 36 of the outer sleeve.

The handle portion 12 includes a trigger piece 38 which is reciprocatingly movably mounted on the housing 18 thereof and which is operable by the surgeon to move the outer sleeve 22 to cover and uncover the sharpened edge 30 of cutting blade and to energize an external motor (not shown) to cause the cutting blade 26 to rotate during a procedure requiring the removal of tissue by morcellation. A drive cable 40 connected to the external motor is connected to the handle portion 12 and is operatively linked to the cutting blade 26 to cause the blade to rotate. A pneumatic tube 42 is connected to a bellows 44 situated within the cavity 20 defined by the handle portion housing 18, which bellows 44 are compressed by the trigger 38 to expel air therefrom and through the pneumatic tube 42 to a sensor on the external drive motor or control circuit therefor to control the energization of the drive motor. The drive cable 40 and pneumatic tube 42 are carried within a sheath 46 coupled to the handle portion 12 of the morcellator.

In FIG. 1, an elongated entry protector member 48 having a conical tip 50 at its distal end 52 that extends beyond the distal end 36 of the outer sleeve 22 is shown mounted on the trocar body portion 10 of the morcellator. The elongated entry protector member 48 is used when inserting the morcellator or trocar body portion 10 thereof through a small incision made in the patient and to prevent or minimize trauma to the surgical site. Once the morcellator and in particular the trocar body portion 10 thereof is properly manipulated in place at the surgical site, the elongated entry protector member 48 is removed from the trocar body portion 10 of the morcellator.

The handle portion 12 further has mounted thereon a push button actuator 54 which may be pressed inwardly by the surgeon to detach the handle portion 12 of the morcellator from the trocar body portion 10, as shown by FIGS. 8-11 of the drawings. The separated trocar body portion 10 is illustrated by FIGS. 12-15 of the drawings. The trocar body portion 10 may remain in place through the incision, and act as a trocar for other laparoscopic instruments during the surgical procedure.

A general description of the various components of the morcellator of the present invention has been described above. A more detailed description of each of the components of the morcellator and in particular the mechanism which allows the handle portion 12 to be detached from the trocar body portion 10 will now be described in greater detail.

Reference should now be made to the cross-sectional and other views of the morcellator shown in FIGS. 3, 4, 7, 9, 11 and 14-24 of the drawings. As mentioned previously, the trocar body portion 10 includes an outer sleeve 22 formed as an elongated tubular member and which defines a bore 24 extending axially along the length thereof. A cutting blade 26 (FIG. 15), also in the form of a tubular member, is situated within the bore 24 of the outer sleeve 22 and rotates therein. The rotatable cutting blade 26 also includes an axial bore 56 for the passage therethrough of morcellated tissue being removed from the patient's body or other laparoscopic instruments, such as a tenaculum used for grasping an anatomical body and directing the body to the sharpened edge 30 of the cutting blade 26, and for removing the transected tissue morsels from the patient's body through the axial bore 56. Alternatively, an inner sleeve 58, also formed as a tubular member, may be situated within the axial bore 56 of the cutting blade 26 so that the cutting blade 26 rotates between the inner sleeve 58 and the outer sleeve 22. The inner sleeve 58, if included, also has an axial bore 60 for the passage of tissue morsels and laparoscopic instruments, such as the tenaculum, therethrough.

The distal end 28 of the cutting blade 26 is formed with a sharpened edge 30 that is covered and uncovered by the outer sleeve 22 to expose at least a portion of the sharpened edge 30 during a surgical procedure involving tissue morcellation. The cutting blade 26 is affixed to a blade gear 62 surrounding the outer surface thereof, which blade gear 62 is driven by a belt 64. The belt 64 also engages a drive gear 66, which has an exposed central opening 68, preferably square in transverse cross-sectional shape. The distal end 70 of a drive cable 40 is removably received by the opening 68 formed in the drive gear 66. The distal end 70 of the drive cable 40 is mounted on the housing 18 of the handle portion 12 and extends therefrom, with the distal end 70 of the cable 40 being complementary shaped to that of the opening 68 formed in the drive gear 66 so that it may be received by the drive gear opening 68 to turn the drive gear 66 without slippage. The proximal end 72 of the drive cable 40 is connected to a motor (not shown) external to the morcellator. The motor, when energized, turns the drive cable 40 which turns the drive gear 66. The drive gear 66 engages the belt 64, which moves the blade gear 62 which, in turn, rotates the cutting blade 26 within the outer sleeve 22.

As also mentioned previously, the trigger piece 38 is reciprocatingly movably mounted on the housing 18 of the handle portion 12 and controls not only the energization of the external drive motor, but also the movement of the outer sleeve 22 to cover and uncover the sharpened edge 30 of the cutting blade 26. The trigger piece 38 is biased outwardly of the housing 18 by a coiled compression spring 74 situated between the trigger piece 38 and an internal tab 76 within the handle portion cavity 20. The trigger piece 38 is normally situated in this outwardly biased position as a safety precaution. In such a position, the sharpened edge 30 of the cutting blade 26 is covered by the outer sleeve 22 of the trocar body portion 10.

As further mentioned previously, the trigger piece 38 engages a pivotal lever arm 78 which, in turn, compresses a bellows 44 situated within the cavity 20 of the handle portion 12, which bellows 44 acts as a pneumatic switch to selectively energize the external motor. The bellows 44 is operatively coupled to a pneumatic tube 42 which extends along the length of the drive cable to the external motor or a controller for the external motor. When the trigger piece 38 is pulled backwardly by the surgeon into the cavity 20 of the handle portion 12 against the force of the spring 74, it compresses the bellows 44 forcing air therefrom through the pneumatic tube 42 to the external motor or controller therefor to energize the motor. When the trigger piece 38 is released by the surgeon, it moves under the force of the spring 74 to its outward position with respect to the handle portion housing 18, and releases pressure on the bellows 44 to deenergize the drive motor, which stops the cutting blade 26 from rotating. The drive cable 40 and the pneumatic tube 42 are covered by a protective sheath 46 extending from the external motor to the housing 18 of the handle portion 12.

As also mentioned previously, the outer sleeve 22 of the morcellator is reciprocatingly slideable a certain distance on the cutting blade 26 to selectively cover and uncover the sharpened edge 30. A collar 80 is affixed to the proximal end 82 of the outer sleeve 22 and surrounds the outer surface thereof. The collar 80 has a flange 84 extending radially outwardly from the outer surface of the collar 30. A semicircular or U-shaped member 86 having two separated, coplanar arms 88 straddles and engages the collar. The U-shaped member 86 has a channel 90 formed in the inner surfaces of the arms, which channel 90 receives therein the flange 84 of the collar 80 to secure the collar 80 thereto, while allowing the collar 80 and the outer sleeve 22 attached thereto to rotate within the U-shaped member 86.

The U-shaped member 86 is biased in the axial direction of the distal end 36 of the outer sleeve 22 by a compression spring 92 situated between and engaging the arms 88 of the member and an internal partial wall 94 of the trocar body portion 10. This ensures that the outer sleeve 22 is biased in a position which covers the sharpened edge 30 of the cutting blade 26, and that pressure must be exerted on the trigger piece 38 to overcome the force of the compression spring 92 to move the U-shaped member 86 and the outer sleeve 22 attached thereto in an opposite direction in order to uncover the sharpened edge 30 of the cutting blade 26.

The U-shaped member 86 includes a leg 96 which extends transversely to the plane in which the arms of the U-shaped member reside. The leg has a free end 98 with a hook 100 projecting transversely therefrom. As will be explained in greater detail, the hook 100 of the U-shaped member is selectively engaged by the hooked end 104 of an elongated arm 102 situated on the handle portion 12 of the morcellator and operatively linked to the trigger piece 38.

The outer sleeve 22 may be rotated on the trocar body portion 10 of the morcellator by the surgeon. The purpose of having the outer sleeve 22 rotatable on the trocar body portion 10 is to allow the selective positioning of an anti-coring device 34 mounted or integrally formed on the distal end 36 of the outer sleeve 22. This device prevents coring into an organ and facilitates the removal of tissue by using the "orange peeling" technique, as is well known in the art.

To rotate the outer sleeve 22 to position the anti-coring device 34, a knob 32 that is graspable by the surgeon is provided. The knob 32 is mounted on the front wall of the housing 14 of the trocar body portion 10. The knob 32 forms part of a hub 106 which surrounds and is affixed to the outer surface of the collar 80 that is mounted on the outer sleeve 22 at the proximal end 82 thereof. More specifically, the knob hub 106 extends through an opening 108 formed in the front wall of the trocar body portion housing 14. The hub 106 has two diametrically opposed pins 110 extending radially outwardly from the inner surface thereof. The pins 110 are received in respective slots 112 formed through the thickness of the collar 80 so that the two components (hub and collar) can rotate together and yet the hub 106 can move axially on the collar 80. An axial side of the hub 106 situated opposite the knob 32 includes an increased diameter flange 114 having a plurality of spaced apart notches 116 formed along the circumference thereof. A projection 118 from the inner surface of the front wall of the housing is selectively received by one of the notches 116 formed in the flange 114. Another compression spring 120 within the cavity 16 of the trocar body portion 10 is situated between and engages the hub 106 and an internal transverse wall 122 of the trocar body portion, exerting pressure on the knob hub 106 to force the hub 106 and in particular the notched flange 114 thereof against the inner surface of the front wall of the trocar body portion housing 14 where the projection 118 is situated. In this position, the projection 118 on the inner surface of the front wall of the housing 118 is received by one of the notches 116 formed in the notched flange 114 to prevent the knob hub 106, the collar 80 and the outer sleeve 22 affixed to the collar 80 from rotating.

When the surgeon wishes to adjust the rotational position of the outer sleeve 22, he grasps the knob 32 and first pushes the knob 32 towards the front wall of the housing 14 against the pressure of the compression spring 120. The notched flange 114 moves axially inwardly away from the inner surface of the front wall of the housing 14 to unseat the projection 118 from a respective notch 116 in the flange 114. Once the notched flange 114 is disengaged from the projection 118 on the inner surface of the front wall, the knob hub 106 is free to rotate, along with the collar 80 and the outer sleeve 22 affixed thereto. The surgeon then turns the knob 32 until the outer sleeve 22 is in a desired position. He then releases pressure on the knob 32. The compression spring 120 forces the notched flange 114 against the inner surface of the front wall of the trocar body portion 10 where the projection 118 will be received by an aligned notch 116 in the flange 114. Slight rotational adjustment of the knob 32 and knob hub 106 may be necessary in order to ensure that the projection 118 is lined up with a notch 116 formed in the flange 114. Once the projection 118 is seated in a notch 116, the knob hub 106, the collar 80 and the outer sleeve 22 attached thereto can no longer rotate on the trocar body portion 10.

When the trocar body portion 10 is detached from the handle 12 and used separately as a trocar, it is desirable to have the outer sleeve 22 locked in a position in which it entirely covers the sharpened edge 30 of the cutting blade 26. For this purpose, a resilient cantilevered leaf spring 124 is provided in the cavity 16 defined by the housing 14 of the trocar body portion 10 which selectively prevents movement of the U-shaped member 86 attached to the collar 80, the collar 80, in turn, being attached to the outer sleeve 22. The leaf spring 124 is affixed at one end to the inside surface of the trocar body portion housing 14, and has a free end 126 which extends into the plane in which the leg of the U-shaped member 86 resides. As stated previously, the leg 96 and the arms 88 of the U-shaped member 86 move reciprocatingly axially within the trocar body portion housing 14 in order to effect the axial movement of the outer sleeve 22 to cover and uncover the sharpened edge 30 of the cutting blade 26. However, if the free end 126 of the cantilevered leaf spring is in the plane of movement of the leg 96 of the U-shaped member 86, the free end 126 will engage the leg 96 of the U-shaped member 86 and prevent its reciprocating movement within the trocar body portion cavity 16. The U-shaped member 86 is biased by the compression spring 92 in the direction of the distal end 36 of the outer sleeve 22 so that the outer sleeve 22 entirely covers the sharpened edge 30 of the cutting blade 26. The resilient leaf spring 124 will be in this position when the handle portion 12 is detached from the trocar body portion 10. In this position, it will block movement of the U-shaped member 86 and the collar 80 attached thereto, and prevent the outer sleeve 22 from being moved to a position where it uncovers the sharpened edge 30 of the cutting blade 26, which could cause inadvertent injury or trauma to the patient. However, when the trocar body portion 10 is mounted on the handle 12, an arm 102 situated on the handle and forming part of the handle detachment mechanism, engages the resilient leaf spring 124 and forces it upwardly out of the plane of movement of the leg 96 of the U-shaped member 86, thereby allowing the U-shaped member 86 to move axially reciprocatingly within the trocar body portion cavity 16. The leaf spring 124 will be deflected by the arm 102 and rides on the upper surface of the arm 102 out of the way of reciprocating movement of the leg 96 of the U-shaped member 86 to allow the surgeon, when pressing on the trigger piece 38, to cover and uncover the sharpened edge 30 of the cutting blade 26, but only when the handle portion 12 of the morcellator is mounted on the trocar body portion 10.

As can be seen from FIGS. 17-23 of the drawings, the mechanism for attaching and detaching the handle portion 12 of the morcellator from the trocar body portion 10, and for effecting movement of the outer sleeve 22 to cover and uncover the sharpened edge 30 of the cutting blade 26, will now be described in detail. The top wall 128 of the handle portion housing 18, where it meets the opposite lateral sidewalls, includes two parallel, elongated L-shaped brackets disposed in mirrored symmetry to face each other. Each elongated L-shaped bracket 130 includes a first leg 132 extending upwardly from the top wall 128 of the handle portion housing 18, and a second leg 134 situated on the first leg and disposed transversely thereto to define a space 136 between the second leg 134 and the outer surface of the top wall 128 of the handle portion. The housing 14 of the trocar body portion 10 has a pair of complementary-shaped rails 138 extending laterally from the bottom wall 140 thereof and spaced below the opposite side walls to define a pair of channels 142 for receiving the second legs 134 of the corresponding elongated L-shaped brackets 130 formed on the handle portion 12. The handle portion 12 is detachably mounted to the trocar body portion 10 by having the rails 138 of the trocar body portion 10 received by and between the elongated L-shaped brackets 130 on the handle portion 12 and by having the second legs 134 of the L-shaped brackets 130 being received by the channels 142 formed in the trocar body portion 10.

Similarly, the trocar body portion housing 14 includes a pair of parallel, elongated L-shaped brackets 144 situated to extend at least partially along the axial length of the bottom wall 140 of the trocar body portion housing 14, with each L-shaped bracket 144 having a first leg 146 extending outwardly from the outer surface of the bottom wall 140, and a second leg 148 situated on the first leg 146 and extending transversely thereto in opposite directions from one another toward their respective opposite lateral sidewalls of the trocar body portion housing 14. Accordingly, the second leg 148 of the L-shaped brackets 144 of the trocar body portion 10 overlies and is spaced from the outer surface of the bottom wall 140 of the trocar body portion 10 to define a space 150 therebetween.

The top wall 128 of the handle portion housing 18 includes a cutout 152 formed through the thickness thereof, the top wall 128 thus being defined with a pair of inner co-planar wall edges 154 that face each other and overhang the cutout 152. When the handle portion 12 is mounted on the trocar body portion 10 of the morcellator, the inner edges 154 of the top wall of the handle portion 12 are received in the spaces 150 defined between the outer surface of the bottom wall 140 of the trocar body portion 10 and the second legs 148 of the elongated L-shaped brackets formed thereon so that the brackets 144 and inner wall edges 154 engage one another to hold the trocar body portion 10 on the handle portion 12. Thus, the inner wall edges 154 and elongated L-shaped brackets 130 of the handle portion 12 respectively engage the elongated L-shaped brackets 144 and rails 142 of the trocar body portion 10 and help secure detachably the handle portion 12 to the trocar body portion 10, with the bottom wall 140 of the trocar body portion 10 facing the top wall 128 of the handle portion 12.

A push button actuator 54 is provided on the morcellator for the surgeon to press to detach the handle portion 12 from the trocar body portion 10. The push button actuator 54 includes a projection 156 exposed through an opening formed through the thickness of the sidewall of the handle portion housing 18. The projection 156 is situated on one leg 158 of a resilient L-shaped member 160 attached to a transversely disposed second leg 162. The second leg 162 has a free end 164 and a tab 166 extending outwardly from an upper surface of the second leg 162 at the free end 164 thereof. The tab 166 resides in the cutout 152 formed in the top wall 128 of the handle portion housing 18.

When the surgeon presses the exposed push button projection 156 on the sidewall of the handle portion housing 18, the tab 166 on the resilient L-shaped member 160 moves inwardly towards the center of the cutout 152 formed in the top wall 128. This tab 166 includes a front face 168 which is ramped or beveled. One of the elongated L-shaped brackets 144 formed on the bottom wall 140 of the trocar body portion 10 includes a notch 170 formed therein. This notch 170 cooperates with the tab 166 on the L-shaped member 160 of the push button actuator 54 such that the tab 166 is received by the notch 170 to secure the handle portion 12 to the trocar body portion 10 of the morcellator. The notched elongated L-shaped bracket 144 on the trocar body portion 10 includes a beveled axial end 172 which cooperates with the beveled face 168 of the tab 166 of the push button actuator 54 to allow the tab 166 to ride along the notched elongated L-shaped bracket 144 and the beveled edge 172 thereof until the tab 166 is resiliently received by the notch 170 formed in the notched L-shaped bracket 144 of the trocar body portion 10.

The exposed projection 156 of the push button actuator 54 on the sidewall of the handle portion 12, when pressed by the surgeon, causes the tab 166 on the actuator to move inwardly of the cutout 152 and out of the notch 170 formed in the notched elongated L-shaped bracket 160 of the trocar body portion 10, thereby disengaging the trocar body portion 10 from the handle portion 12 to allow the handle portion 12 to be removed from the trocar body portion 10. It is envisioned to be within the scope of the present invention to reverse the described positions of the push button actuator 54 and the notched elongated L-shaped bracket 144 such that the actuator 54 with its exposed push button projection 156 and its tab 166 are situated on the trocar body portion 10, and one of the L-shaped brackets 130 on the handle portion 12 is notched to selectively receive the tab 166 of the actuator 54 to attach and detach the handle portion 12 from the trocar body portion 10.

An elongated arm 102 extends axially along the top wall 128 of the handle portion 12 and is situated within the cutout 152 formed therein. One axial end of the arm includes a first pin 174 extending outwardly from a first sidewall thereof. A linkage 176 is pivotally joined to the first pin 174 at one end of the linkage. The other end of the linkage 176 is pivotally joined to a second pin 178 which rides within a camming slot 180 formed through the thickness of a wall of the trigger piece 38. Movement of the trigger piece 38 reciprocatingly on the handle portion 12 causes the second pin 178 on one end of the linkage 176 to ride within and follow the particular contour of the camming slot 180. This, in turn, causes the linkage 176 to force the arm 102 to move axially on the handle portion 12 within the cutout 152 formed in the top wall 128 thereof due to the connection of the linkage 176 to the first pin 174 on one end of the arm 102.

The opposite axial end of the arm 102 includes a hook 104 or projection extending from a sidewall thereof. When the handle portion 12 is attached to the trocar body portion 10, the hooked end 104 of the arm 102 of the handle portion 12 engages the hook 100 of the U-shaped member 86 joined to the collar 80 on the trocar body portion 10, which allows the outer sleeve 22 to move reciprocatingly on the cutting blade 26 to uncover and cover the sharpened edge 30 of the cutting blade 26 when the surgeon presses on or releases the trigger piece 38 on the handle portion 12.

More specifically, when the surgeon presses on the trigger piece 38 to move the trigger piece 38 inwardly on the handle portion housing 18, the linkage 176 pivotally attached between the trigger piece 38 and the arm 102 causes the arm 102 to move backward away from the sharpened edge 30 of the cutting blade 26. The hooked end 104 of the arm 102 engages the hook 100 on the U-shaped member 86 and pulls the U-shaped member 86 in the same direction away from the sharpened edge 30 of the cutting blade 26. The U-shaped member 86 is attached to the collar 80 affixed to the outer sleeve 22 and, therefore, causes the outer sleeve 22 to move on the cutting blade 26 and fully or at least partially uncover the sharpened edge 30 thereof.

When the surgeon releases the trigger piece 38, the trigger piece 38 moves outwardly of the handle portion housing 18 due to the force of the compression spring 74. The linkage 176 between the trigger piece 38 and the arm 102 causes the arm 102 to move forward, that is, in the direction of the sharpened edge 30 of the cutting blade 26. The arm 102, through the engagement of its hooked end 104 with the hook 100 on the U-shaped member 86, allows the U-shaped member 86 to return to its original position within the trocar body portion cavity 16 under the force of its compression spring 92. This, in turn, allows the collar 80 and the outer sleeve 22 attached thereto to move in the opposite direction on the cutting blade 26 to cover the sharpened edge 30 thereof. It should be understood that the outer sleeve 22 generally includes the anti-coring device 34 as a sub-component thereof, and therefore, when it is stated herein that the outer sleeve covers or at least partially uncovers the sharpened edge 30 of the cutting blade 26, what is meant is that the outer sleeve 22 or its anti-coring device 34 covers or at least partially uncovers the sharpened edge 30.

When the surgeon pushes on the push button projection 156 located on the sidewall of the handle portion 12, the movement of the actuator 54 not only causes the tab 166 on the L-shaped member 160 to move out of the notch 170 formed in the notched elongated L-shaped bracket 144 of the trocar body portion 10, but also causes the tab 166 to engage a second sidewall 182 of the arm 102, causing the hooked end 104 of the arm 102 to move in a first lateral direction. When the arm 102 moves laterally, its hooked end 104 disengages the hook 100 of the U-shaped member 86 so that the handle portion 12 may be fully detached from the trocar body portion 10 of the morcellator.

The arm 102 also includes a resilient, cantilevered spring member 184 extending from the first sidewall 186 thereof. The resilient, cantilevered spring member 184 engages the opposite elongated L-shaped bracket 144 of the trocar body portion 10 not having the notch, in order to bias the arm 102 in an opposite, second lateral direction in which its hooked end 104 will engage the hook 100 of the U-shaped member 86. The resilient, cantilevered spring member 184 also forces the arm 102 to a lateral position where it is in proximity to the tab 166 of the push button actuator 54 so that the tab 166 can engage the first sidewall 186 of the arm 102 to disengage the hooked end 104 of the arm 102 from the U-shaped member 86.

Another important safety feature of the morcellator of the present invention is to prevent the detachment of the handle portion 12 from the trocar body portion 10 when the trigger piece 38 is being pressed by the surgeon, which action, as described previously, retracts the outer sleeve 22 to uncover the sharpened edge 30 of the cutting blade 26 and which energizes the motor when the trigger piece 38 is fully pressed into the housing 18 of the handle portion 12. To prevent the detachment of the handle portion 12 from the trocar body portion 10 when the trigger piece 38 is being pressed, the arm 102 includes a widened plate 186 situated on its bottom surface over a portion of the axial length thereof. Furthermore, a post 190 extends inwardly of the handle portion cavity 20 from the inner surface of a sidewall of the handle portion 12 opposite to and in alignment with the tab 166 formed on the push button actuator 54. The spacing between the tip of the post 190 and the tab 166 of the push button actuator 54 is equal to or slightly greater than the width of the plate 188 situated on the arm 102 so that the arm 102 may move freely reciprocatingly in the axial direction of the handle 12 between the tab 166 and the post 190. Furthermore, when the trigger piece 38 is not pressed and is in its most outward position with respect to the handle portion housing 18, the arm plate 190 is not situated between the tab 166 and the post 190; rather, a narrower portion 192 of the arm 102 is situated therebetween. This allows the arm 102 to move laterally when engaged by the tab 166 of the push button actuator 54 to disengage its hooked end 104 from the hook 100 of the U-shaped member 86, and further allows the tab 166 to move out of the notch 170 formed in the notched elongated L-shaped bracket 160 of the trocar body portion 10, when it is desired to separate the trocar body portion 10 from the handle portion 12.

However, when the trigger piece 38 is slightly pressed by the surgeon, the linkage 176 between the trigger piece 38 and the arm 102 moves the arm 102 backward on the handle portion 12 such that the widened plate 188 of the arm 102 is now interposed between the tab 166 of the push button member 156 and the post 190. The width of the arm plate 188 is slightly less than or equal to the distance between the tip of the post 190 and the tab 166 on the push button actuator 54 such that the tab 166 on the push button actuator 54 cannot move within the cutout 152 to unseat itself from the notch 170 formed in the notched elongated L-shaped bracket 144 of the trocar body portion 10, nor can it deflect the arm 102 laterally to disengage the hooked end 104 of the arm 102 from the hook 100 of the U-shaped member 86 of the trocar body portion 10 that controls movement of the outer sleeve 22. Accordingly, the handle portion 12 cannot be removed from the trocar body portion 10, nor will the arm 102 disengage from the U-shaped member 86, when the trigger piece 38 is moved preferably by even a slight amount by the surgeon.

As mentioned earlier, there is a resilient, cantilevered leaf spring 124 within the cavity 16 of the trocar body portion 10 that prevents the U-shaped member 86 from moving axially within the cavity 16 of the trocar body portion 10 when the handle portion 12 is detached from the trocar body portion 10. However, when the handle portion 12 is attached to the trocar body portion 10, the cantilevered leaf spring 124 is deflected by the arm 102 of the handle portion 12 and is forced out of the plane of movement of the leg 96 of the U-shaped member 86 by riding on the top surface of the arm 102, and allows the arm 102 to move the U-shaped member 86 axially within the trocar body portion 10, thus permitting the outer sleeve 22 to move reciprocatingly on the cutting blade 26 to cover and uncover the sharpened edge 30 thereof.

There are a number of additional features of the morcellator of the present invention besides having a detachable handle portion 12 so that the trocar body portion 10 thereof may be used separately with other surgical instruments during a procedure. For example, the morcellator includes vacuum release holes 194 formed through the thickness of the sidewall of the outer sleeve 22. Preferably, two small holes are placed one hundred, eighty degrees (180°) apart on diametrically opposite sides of the sidewall of the outer sleeve 22, and are positioned approximately 0.250 inches from the distal end 36 of the outer sleeve 22. This particular distance from the distal end 36 of the sleeve 22, as well as having the holes 194 on both sides of the outer sleeve 22, ensure that one or both of the holes 194 will not be blocked by the abdominal wall or by tissue in the patient's body cavity. The vacuum release holes 194 are in communication with the axial bores of the outer sleeve 22, the cutting blade 26 and the inner sleeve 58, if the inner sleeve 58 is included. While withdrawing tissue or instruments through the trocar body portion 10 of the morcellator, the holes 194 prevent a build up of negative pressure in the axial bore of either the cutting blade 26 or the inner sleeve 58, if such is provided, which could otherwise have caused transected tissue being withdrawn through the trocar body portion 10 of the morcellator using a tenaculum or the like to become dislodged from the tenaculum and entrapped within the morcellator, possibly requiring the removal of the morcellator from the incision.

The morcellator of the present invention further includes a low drag seal system. Because the trocar body portion 10, without the handle portion 12 of the morcellator, may be used and serve as a trocar for other surgical instruments, the seal system used therein allows for the fine manipulation of such instruments as well as a relatively large range of instrumentation diameters. As can be seen from FIG. 24 of the drawings, the proximal end 198 of the inner sleeve 58 is connected to a duck bill seal 196 or flippable "toilet seat" seal such as the Endopath™ Multiseal™ seal manufactured by Johnson & Johnson Gateway, LLC of Piscataway, N.J. and having Part No. MS512 or MS712, for example, which is in communication with a surgical trocar reducer cap 200, such as the Endopath™ reducer having Part No. R1805 or R1810, also manufactured by Johnson & Johnson Gateway, LLC. This particular low drag seal system allows the trocar body portion 10 of the morcellator to be used with most surgical instruments for ease and convenience, while providing low friction to transected tissues being removed through the trocar body portion 10 during a surgical procedure requiring morcellation. The seal system of the morcellator furthermore will maintain pneumoperitineum of the patient's body cavity when used during a morcellation procedure or when the trocar body portion 10 is used separately as a trocar for other surgical instruments.

Furthermore, the morcellator of the present invention preferably has a shorter working body. The length of the trocar body portion 10 is preferably between about 125 millimeters and 135 millimeters. This is significantly shorter than many morcellators currently used today, and allows the trocar body portion 10 of the morcellator to be used separately and serve as a trocar for use with operating instruments that have lengths which are shorter than those of conventional morcellators. The preferred length of the trocar body portion 10 of the morcellator mentioned above is chosen to allow the morcellator to be used with obese patients and to provide a short enough length so that other surgical instruments will extend a sufficient distance past the distal end of the trocar body portion 10 to be useable therewith.

The surgical morcellator of the present invention overcomes many inherent disadvantages of currently used morcellators. By allowing the handle portion 12 to be removed, the device is less bulky and removes the drag and pull of the drive cable 40. The trocar body portion 10, used separately from the handle portion 12, can be manipulated more accurately by the surgeon during a procedure, and the trocar body portion 10 will remain anchored through the abdominal wall incision without having to be held or supported by the surgeon. Conventional morcellating devices need to be held at all times due to the weight of the device and the drag of the cable.

Additionally, the handle portion 12 is interlocked so that it can only be removed when the sharpened edge 30 of the cutting blade 26 is shielded by the outer sleeve 22. This prevents inadvertent injury to the patient and trauma at the surgical site. The trocar body portion 10 of the morcellator, when used separately from the handle portion 12 and the drive cable 40 attached thereto, is relatively lightweight, and can serve as an entry port for other instruments when morcellation is not required. Furthermore, current surgical techniques involve the steps of performing morcellation, removing the morcellator and inserting a trocar through the existing incision so that other surgical instruments may be used, and possibly removing the trocar and reinserting the morcellating device to perform further morcellation at the end of the procedure, which no longer are required to be done with the morcellator of the present invention; the relatively lightweight, trocar body portion 10 of the present invention may remain in place through the existing incision during non-morcellation stages of the surgery, or the handle portion 12 may be reattached to the trocar body portion 10 if further morcellation is required. Thus, the surgical procedure may advance at a greater speed with less trauma to the incision site through fewer reinsertions of different surgical instruments. This reduces the need for different surgical instrumentation, and further reduces the cost for each surgery.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A surgical morcellator, which comprises:

a trocar body portion, the trocar body portion having an outer sleeve formed as an elongated tubular member and which defines a bore extending axially along the length thereof, and a cylindrical cutting blade, the cylindrical cutting blade being in the form of a tubular member and situated within the bore of the outer sleeve, the cylindrical cutting blade having a distal end and formed with a sharpened edge situated at the distal end thereof, the cylindrical cutting blade being rotatable within the bore of the outer sleeve, the outer sleeve being axially movable relative to the cylindrical cutting blade between a first position in which the outer sleeve covers the sharpened edge of the cylindrical cutting blade and a second position in which the outer sleeve uncovers the sharpened edge of the cylindrical cutting blade;

a handle portion detachably mounted to the trocar body portion, the handle portion having a trigger piece movably mounted thereon, the trigger piece being operatively coupled to the outer sleeve to effect the selective axial movement of the outer sleeve to cover and uncover the sharpened edge of the cylindrical cutting blade, wherein the cylindrical cutting blade is rotatable relative to the outer sleeve when the handle portion is mounted to the trocar body portion; and a handle portion detachment mechanism situated on at least one of the trocar body portion and the handle portion, the handle portion detachment mechanism selectively detachably mounting the handle portion to the trocar body portion such that when the handle portion is detached from the body portion, the bore of the trocar body portion is accessible by a user and capable of receiving therein surgical instruments;

an outer sleeve locking mechanism in physical communication with the outer sleeve and trocar body portion that prevents movement of the outer sleeve from the first position to the second position when the handle is detached from the trocar body portion; and the handle portion including a drive cable adapted to drive rotation of the cylindrical cutting blade, the drive cable being coupled with the cylindrical cutting blade when the handle portion is mounted to the trocar body portion and decoupled from the cylindrical cutting blade when the handle portion is detached from the trocar body portion.

2. A surgical morcellator as defined by claim 1, wherein the handle portion detachment mechanism includes:

at least one first member situated on the handle portion; and at least one second member situated on the trocar body portion, the at least one first member of the handle portion selectively cooperatively engaging the at least one second member on the trocar body portion for detachably mounting the handle portion on the trocar body portion;

means for selectively preventing the disengagement of the at least one first member from the at least one second member, and wherein the outer sleeve locking mechanism is a resilient spring.

3. A surgical morcellator as defined by claim 1, wherein the handle portion detachment mechanism includes:

at least one elongated first member situated on the handle portion;

at least one elongated second member situated on the trocar body portion, the at least one elongated first member on the handle portion slidably engaging the at least one second member on the trocar body portion, at least one of the at least one elongated first member and the at least one elongated second member having a notch formed therein; and a push button actuator, the push button actuator being mounted on at least one of the handle portion and the trocar body portion, the push button actuator including a push button projection mounted thereon for pressing by a user of the morcellator, and a tab mounted thereon, the tab being selectively received by the notch formed in the at least one of the at least one elongated first member and the at least one elongated second member.

4. A surgical morcellator as defined by claim 1, wherein the handle portion detachment mechanism includes:

a pair of parallelly disposed, elongated first members situated on the handle portion;

a pair of parallelly disposed, elongated second members situated on the trocar body portion, the pair of elongated second members cooperatingly engaging the pair of elongated first members to detachably secure the handle portion to the trocar body portion, one elongated second member of the pair of elongated second members having a notch formed therein; and a push button actuator, the push button actuator being mounted on the handle portion, the push button actuator including a push button projection mounted thereon for pressing by a user of the morcellator, and a tab mounted thereon, the tab being selectively received by the notch formed in the one elongated second member.

5. A surgical morcellator as defined by claim 1, wherein trigger piece is engageable to energize an external motor to cause the cylindrical cutting blade to rotate within the outer sleeve for morcellating tissue.

6. A surgical morcellator as defined by claim 1, wherein the cylindrical cutting blade includes an axial bore for the passage therethrough of morcellated tissue.

7. A surgical morcellator as defined by claim 1, wherein the trocar body portion includes a housing, and wherein the outer sleeve is selectively rotatable relative to the housing of the trocar body portion.

8. A surgical morcellator as defined by claim 7, wherein the trocar body portion further comprises a knob coupled with the outer sleeve and the housing of the trocar body portion, wherein the knob is engageable for selectively rotating the outer sleeve relative to the housing of the trocar body portion.

9. A surgical morcellator, which comprises:

a trocar body portion, the trocar portion including a cylindrical outer sleeve, the outer sleeve having a bore formed axially therethrough, and a cylindrical cutting blade, the cylindrical cutting blade having an axial distal end and a sharpened edge situated at the distal end, the cutting blade being received by the axial bore of the outer sleeve and being rotatable therein, the outer sleeve being reciprocatingly slidable axially on the cutting blade selectively to cover and at least partially uncover the sharpened edge of the cutting blade; and a handle portion, the handle portion being mounted on the trocar body portion, the handle portion having a trigger piece movably mounted therein, the trigger piece being operatively coupled to the outer sleeve to effect the selective axial movement of the outer sleeve to cover and at least partially uncover the sharpened edge of the cutting blade;

wherein the outer sleeve includes a distal end and a proximal end situated axially opposite the distal end, the distal end of the outer sleeve being situated in proximity to the distal end of the cutting blade, the proximal end of the outer sleeve being attached to the trocar body portion;

wherein the trocar body portion further includes a housing, the housing having a front wall and an opening formed through the thickness of the front wall, the proximal end of the outer sleeve being received by the opening in the front wall of the housing, a collar mounted on the proximal end of the outer sleeve, and a rotatable knob operatively coupled to the collar, whereby rotation of the knob by the user of the morcellator effects rotation of the collar and the outer sleeve on which the collar is mounted;

wherein the trocar body portion further includes a hub, the hub being concentrically mounted on the collar, the knob being attached to the hub, the hub being operatively coupled to the collar and being rotatable with the collar and axially moveable on the collar;

wherein the housing of the trocar body portion defines an internal cavity;

wherein the hub includes a first end and a second end situated axially opposite the first end, the knob being mounted on the first end of the hub and situated outside the trocar body portion housing at the front wall thereof, the hub further including a circular flange having a plurality of spaced apart openings formed circumferentially therein, the circular flange being situated with the cavity of the trocar body portion;

wherein the trocar body portion includes at least one projection situated within the cavity thereof, the at least one projection being received by at least one of the openings formed in the flange to selectively prevent rotational movement of the hub, the collar on which the hub is mounted and the outer sleeve on which the collar is mounted;

wherein the trocar body portion further includes a first compression spring, the first compression spring engaging the hub to bias the hub to a first axial position in which the at least one projection is received by the at least one of the openings in the hub, the hub being axially moveable on the collar and positionable thereon against the bias of the first compression spring in a second position in which the at least one projection is unseated from the at least one of the openings in the hub to allow the hub, the collar on which the hub is mounted and the outer sleeve on which the collar is mounted to rotate upon the user of the morcellator rotating the knob;

wherein the trocar body portion includes a U-shaped member, the U-shaped member having a pair of spaced apart arms, the collar being situated between the arms, the arms being operatively coupled to the collar, the U-shaped member being axially moveable on the trocar body portion such that axial movement of the U-shaped member effects axial movement of the collar and axial movement of the outer sleeve on which the collar is mounted, the trigger piece of the handle portion being operatively coupled to the U-shaped member to effect axial movement thereof;

wherein the collar includes a flange extending radially outwardly therefrom;

wherein each of the spaced apart arms of the U-shaped member has a channel of the other arm of the spaced apart arms, the flange of the collar being received by the channels of the spaced apart arms and being slidable therein to allow the collar to rotate on the U-shaped member; and wherein the trocar body portion includes a second compression spring, the second compression spring engaging the U-shaped member to bias the U-shaped member in a first axial position in which the outer sleeve on which the collar attached to the U-shaped member is mounted is covering the sharpened edge of the cutting blade, the U-shaped member being axially moveable on the trocar body portion and positionable thereon against the bias of the second compression spring in a second position in which the outer sleeve is at least partially uncovering the sharpened edge of the cutting blade.

10. A surgical morcellator as defined by claim 9, wherein the U-shaped member includes a leg extending therefrom, the leg having a free end and a hook projecting from the free end; and wherein the handle portion includes an elongated arm, the arm being operatively coupled to the trigger piece and moving reciprocatingly in response to movement of the trigger piece, the arm having a hooked free end, the hooked free end selectively engaging the hook of the leg of the U-shaped member to effect movement of the U-shaped member and the outer sleeve operatively coupled thereto upon movement of the trigger piece.

11. A surgical morcellator as defined by claim 10, wherein the handle portion is detachably mounted on the trocar body portion; and wherein the surgical morcellator further comprises a handle portion detachment mechanism situated on the trocar body portion and the handle portion, the handle portion detachment mechanism detachably mounting the handle portion to the trocar body portion.

12. A surgical morcellator as defined by claim 11, wherein the handle portion detachment mechanism includes:

at least one elongated first member situated on the handle portion;

at least one elongated second member situated on the trocar body portion, the at least one elongated first member on the handle portion engaging the at least one second member on the trocar body portion, at least one of the at least one elongated first member and the at least one elongated second member having a notch formed therein; and a push button actuator, the push button actuator being mounted on at least one of the handle portion and the trocar body portion, the push button actuator including a push button projection mounted thereon for pressing by a user of the morcellator, and a tab mounted thereon, the tab being selectively received by the notch formed in the at least one of the at least one elongated first member and the at least one elongated second member.

13. A surgical morcellator as defined by claim 11, wherein the handle portion detachment mechanism includes:

a pair of parallelly disposed, elongated first members situated on the handle portion;

a pair of parallelly disposed, elongated second members situated on the trocar body portion, the pair of elongated second members cooperatively engaging the pair of elongated first members to detachably secure the handle portion to the trocar body portion, one elongated second member of the pair of elongated second members having a notch formed therein; and a push button actuator, the push button actuator being mounted on the handle portion, the push button actuator including a push button projection mounted thereon for pressing by a user of the morcellator, and a tab mounted thereon, the tab being selectively received by the notch formed in the one elongated second member.

14. A surgical morcellator as defined by claim 13, wherein the arm is selectively moveable transversely; and wherein the tab of the push button actuator selectively engages the arm to move the arm transversely, the arm being moveable transversely between a first position in which the hooked end thereof engages the hook of the leg of the U-shaped member to effectively operatively couple the trigger piece to the U-shaped member whereby movement of the trigger piece effects movement of the outer sleeve to cover and at least partially uncover the sharpened edge of the cutting blade, and a second position in which the hooked end of the arm is disengaged from the hook of the leg of the U-shaped member to effectively operatively decouple the trigger piece from the U-shaped member to allow the handle portion to be detached from the trocar body portion.

15. A surgical morcellator as defined by claim 14, wherein the trocar body portion further includes a resilient leaf spring, the leaf spring being in a biased first position in which the leaf spring is engageable with the U-shaped member to prevent axial movement thereof and to prevent the outer sleeve from at least partially uncovering the sharpened edge of the cutting blade when the handle portion is detached from the trocar body portion, the leaf spring engaging and being deflected by the arm to a second position in which the leaf spring is disengageable with respect to the U-shaped member to allow the axial movement thereof and to allow the outer sleeve to at least partially uncover the sharpened edge of the cutting blade when the handle portion is mounted on the trocar body portion.

* * * * *